(12) United States Patent
Llop et al.

(10) Patent No.: US 10,278,789 B2
(45) Date of Patent: May 7, 2019

(54) BONE FOUNDATION GUIDE SYSTEM AND METHOD

(71) Applicant: NATIONAL DENTEX, LLC, Palm Beach Gardens, FL (US)

(72) Inventors: Daniel R. Llop, Reno, NV (US);
Armand C. Jusuf, Reno, NV (US);
Ryan A. Spanke, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 357 days.

(21) Appl. No.: 15/062,109

(22) Filed: Mar. 5, 2016

(65) Prior Publication Data
US 2017/0112591 A1  Apr. 27, 2017
US 2017/0281307 A9  Oct. 5, 2017

Related U.S. Application Data

(63) Continuation-in-part of application No. 14/921,111, filed on Oct. 23, 2015, which is a continuation-in-part
(Continued)

(51) Int. Cl.
*A61C 1/08* (2006.01)
*A61C 8/00* (2006.01)
(Continued)

(52) U.S. Cl.
CPC .............. *A61C 1/084* (2013.01); *A61C 1/085* (2013.01); *A61C 8/0027* (2013.01);
(Continued)

(58) Field of Classification Search
CPC ...... A61C 1/084; A61C 8/0089; A61C 8/0006
(Continued)

(56) References Cited

U.S. PATENT DOCUMENTS 5,018,970 A   5/1991 Stordahl
5,725,376 A   3/1998 Poirier
(Continued)

FOREIGN PATENT DOCUMENTS

CA   2795668 A1   11/2011
CA   2934371 A1   6/2015
(Continued)

OTHER PUBLICATIONS

Online video of zygomatic dental implant surgery: http://www.youtube.com/watch?v=TGBxbP9aa2g&sns=em Title Zygomatic Implant Guided Surgery—Noris Medical, Published on Mar. 11, 2015, 1 pg.
(Continued)

*Primary Examiner* — Heidi M Eide
*Assistant Examiner* — Mirayda A Aponte
(74) *Attorney, Agent, or Firm* — Frost Brown Todd LLC

(57) ABSTRACT

A bone foundation guide system has a bone foundation guide including a body that is contoured to reversibly affix to a bone segment of a dental implant surgical site. The body is further contoured to guide the cutting of a portion of the bone segment from a dental implant surgical site and alternatively support a dental implant surgical guide. The body is further contoured to support a bone foundation guide prosthesis as an alternative to the dental implant surgical guide. The bone foundation guide prosthesis combines with the body to accommodate the bone segment portion as placed through the body prior to the bone segment portion being removed from the dental implant site through the use of the body.

17 Claims, 17 Drawing Sheets

Related U.S. Application Data of application No. 14/214,555, filed on Mar. 14, 2014.

(60) Provisional application No. 61/784,029, filed on Mar. 14, 2013.

(51) Int. Cl.
*A61C 19/05* (2006.01)
*A61C 8/02* (2006.01)

(52) U.S. Cl.
CPC ............ *A61C 8/0089* (2013.01); *A61C 19/05* (2013.01); *A61C 8/0006* (2013.01)

(58) Field of Classification Search
USPC .......................................................... 433/72
See application file for complete search history.

(56) References Cited

U.S. PATENT DOCUMENTS

| | | | |
|---|---|---|---|
| 5,967,777 A | 10/1999 | Klein et al. | |
| 6,319,006 B1 | 11/2001 | Scherer et al. | |
| 6,382,975 B1 | 5/2002 | Poirier | |
| 6,491,696 B1 | 12/2002 | Kunkel | |
| 6,672,870 B2 | 1/2004 | Knapp | |
| 6,814,575 B2 | 11/2004 | Poirier | |
| 6,997,707 B2 | 2/2006 | Germanier | |
| 7,331,786 B2 | 2/2008 | Poirier | |
| 7,632,097 B2 | 12/2009 | De Clerck | |
| 7,774,084 B2 | 8/2010 | Cinader, Jr. | |
| 7,824,181 B2 | 11/2010 | Sers | |
| 7,866,980 B2 | 1/2011 | Poirier | |
| 7,887,327 B2 | 2/2011 | Marotta | |
| 7,905,726 B2 | 3/2011 | Stumpel | |
| 7,909,606 B2 | 3/2011 | Marcello | |
| 7,942,668 B2 | 5/2011 | Brajnovic et al. | |
| 8,011,927 B2 | 9/2011 | Berckmans, III et al. | |
| 8,021,153 B2 | 9/2011 | Poirier | |
| 8,038,440 B2 | 10/2011 | Swaelens et al. | |
| 8,135,492 B2 | 3/2012 | Yau et al. | |
| 8,142,189 B2 | 3/2012 | Brajnovic | |
| 8,352,060 B2 | 1/2013 | Chun et al. | |
| 8,364,301 B2 | 1/2013 | Schmitt | |
| 8,371,849 B2 | 2/2013 | Gao | |
| 8,529,255 B2 | 9/2013 | Poirier et al. | |
| 8,540,510 B2 | 9/2013 | Brajnovic | |
| 8,574,302 B2 | 11/2013 | McKay | |
| 8,585,402 B2 | 11/2013 | Vogel et al. | |
| 8,706,672 B2 | 4/2014 | Malfliet et al. | |
| 8,770,972 B2 | 7/2014 | Swaelens et al. | |
| 8,777,612 B2 | 7/2014 | Suttin et al. | |
| 8,827,699 B2 | 9/2014 | Bavar | |
| 8,899,984 B2 | 12/2014 | Llop et al. | |
| 9,069,914 B2 | 6/2015 | Kopelman et al. | |
| 9,107,723 B2 | 8/2015 | Hall et al. | |
| 9,155,548 B2 | 10/2015 | Lin | |
| 9,155,599 B2 | 10/2015 | Thompson et al. | |
| 9,161,822 B2 | 10/2015 | Stevens et al. | |
| 9,168,112 B2 | 10/2015 | Haber | |
| 9,173,723 B2 | 11/2015 | Harrison | |
| 9,211,165 B2 | 12/2015 | Jamison | |
| 9,226,801 B2 | 1/2016 | Groscurth et al. | |
| 9,259,291 B2 | 2/2016 | Gantes | |
| 9,308,055 B2 | 4/2016 | Fisker et al. | |
| 9,336,336 B2 | 5/2016 | Deichmann et al. | |
| 9,358,082 B2 | 6/2016 | Nilsson | |
| 9,381,072 B2 | 7/2016 | Furrer et al. | |
| 9,402,698 B2 | 8/2016 | Thompson et al. | |
| 9,408,678 B2 | 8/2016 | Harrison | |
| 9,498,307 B2 | 11/2016 | Harrison | |
| 9,504,533 B2 | 11/2016 | Groscurth et al. | |
| 2006/0166169 A1 | 7/2006 | Dawood | |
| 2007/0162014 A1 | 7/2007 | Campbell et al. | |
| 2009/0092948 A1 | 4/2009 | Gantes | |
| 2009/0274990 A1 | 11/2009 | Kim | |
| 2009/0298008 A1 | 12/2009 | Groscurth et al. | |
| 2010/0035201 A1 | 2/2010 | Beck et al. | |
| 2010/0124731 A1 | 5/2010 | Groscurth et al. | |
| 2010/0316974 A1 | 12/2010 | Yau et al. | |
| 2011/0033819 A1 | 2/2011 | Freyer et al. | |
| 2011/0045431 A1 | 2/2011 | Groscurth et al. | |
| 2011/0045432 A1 | 2/2011 | Groscurth et al. | |
| 2011/0111371 A1 | 5/2011 | Haber | |
| 2011/0151399 A1 | 6/2011 | De Clerck et al. | |
| 2011/0256508 A1 | 10/2011 | Gantes | |
| 2012/0046914 A1 | 2/2012 | Gao | |
| 2012/0053593 A1 | 3/2012 | Abboud | |
| 2012/0156638 A1 | 6/2012 | Gantes | |
| 2012/0261848 A1 | 10/2012 | Haraszati | |
| 2012/0277899 A1 | 11/2012 | Chun et al. | |
| 2013/0011813 A1 | 1/2013 | Garcia et al. | |
| 2013/0023888 A1 | 1/2013 | Choi et al. | |
| 2013/0209956 A1 | 8/2013 | Sanders | |
| 2013/0252202 A1 | 9/2013 | Pardeller et al. | |
| 2014/0026419 A1 | 1/2014 | Haber | |
| 2014/0080086 A1 | 3/2014 | Chen | |
| 2014/0080092 A1 | 3/2014 | Suttin et al. | |
| 2014/0099600 A1* | 4/2014 | Harrison ................ A61C 8/005 433/173 |
| 2014/0255873 A1 | 9/2014 | Bullis et al. | |
| 2014/0255876 A1 | 9/2014 | Alpern et al. | |
| 2014/0272778 A1 | 9/2014 | Llop | |
| 2014/0272779 A1 | 9/2014 | Okay | |
| 2014/0272780 A1 | 9/2014 | Llop | |
| 2015/0010881 A1 | 1/2015 | Llop | |
| 2015/0025855 A1 | 1/2015 | Fisker et al. | |
| 2015/0030995 A1 | 1/2015 | Villa | |
| 2015/0037756 A1 | 2/2015 | Berckmans, III et al. | |
| 2015/0093717 A1 | 4/2015 | Ali | |
| 2015/0111179 A1 | 4/2015 | Suttin | |
| 2015/0133956 A1 | 5/2015 | Dayan et al. | |
| 2015/0150684 A1 | 6/2015 | De Clerck | |
| 2015/0230894 A1 | 8/2015 | Juzbasic et al. | |
| 2015/0265372 A1 | 9/2015 | Kim et al. | |
| 2015/0272704 A1 | 10/2015 | Watson et al. | |
| 2015/0272705 A1 | 10/2015 | Watson et al. | |
| 2015/0302170 A1 | 10/2015 | Berckmans, III et al. | |
| 2015/0359614 A1 | 12/2015 | Sachdeva et al. | |
| 2015/0374460 A1 | 12/2015 | Sachdeva et al. | |
| 2016/0008110 A1 | 1/2016 | Harrison | |
| 2016/0038255 A1 | 2/2016 | Llop | |
| 2016/0106517 A1 | 4/2016 | Groscurth et al. | |
| 2016/0106518 A1 | 4/2016 | Choi et al. | |
| 2016/0128810 A1 | 5/2016 | Fostick et al. | |
| 2016/0157967 A1 | 6/2016 | Kim et al. | |
| 2016/0157970 A1 | 6/2016 | Gantes | |
| 2016/0278878 A1 | 9/2016 | Watson et al. | |
| 2016/0287336 A1 | 10/2016 | Kim et al. | |
| 2016/0324599 A1 | 11/2016 | Harrison | |
| 2016/0045280 A1 | 12/2016 | Haber | |
| 2017/0071697 A1 | 3/2017 | Groscurth et al. | |
| 2017/0112592 A1 | 4/2017 | Groscurth et al. | |
| 2017/0252126 A1 | 9/2017 | Llop | |

FOREIGN PATENT DOCUMENTS

| | | | | |
|---|---|---|---|---|
| EP | 2425797 A1 * | 3/2012 | ............ | A61C 1/084 |
| MX | 2014001163 A | 7/2015 | | |
| WO | WO 2010/061391 | 6/2010 | | |
| WO | WO 2012/007615 | 1/2012 | | |
| WO | WO-2013181721 A2 * | 12/2013 | ........... | A61F 2/2803 |
| WO | WO 2014/130536 | 8/2014 | | |
| WO | WO 2015/148891 | 10/2015 | | |

OTHER PUBLICATIONS

Select pages showing a bone reduction guide from the publication Art of Computer Guided Implantology by Tradiev and Rosenfield, Copyright 2009, 3 pgs.

Website showing a bone reduction guide that was uploaded by www.dentalinformation.com on Aug. 4, 2011 located at https://www.youtube.com/watch?v=AZnReFZmLN8 the upload is entitled

(56) References Cited

OTHER PUBLICATIONS

Bone Reduction and Bone Supported Guide for Guided Dental Implant Surgery, 1 pg.
International Search Report and Written Opinion dated Mar. 2, 2016 for Application No. PCT/US2015/061002, 14 pgs.
International Search Report and Written Opinion dated Jul. 26, 2016 for Application No. PCT/US2016/021097, 13 pgs.
International Search Report and Written Opinion dated Jun. 16, 2017 for Application No. PCT/US2017/020746, 13 pgs.
International Search Report and Written Opinion dated Dec. 28, 2017 for Application No. PCT/US2017/054804, 10 pgs.

* cited by examiner

BONE FOUNDATION GUIDE SYSTEM AND METHOD

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to dental implant and surgical guides. More particularly to those bone modification guides that support a dental implant surgical guide.

BACKGROUND

As a person ages, they generally incur tooth and bone loss requiring prosthetic replacement as provided by the dental profession. One of the more important aspects of this replacement procedure is the need to solidly anchor within the available bone structure those implants used to secure individual (replacement artificial tooth) or collective (e.g., denture) dental prosthetic. When teeth lose bone around their roots, the bone (e.g., mandibular strut or the maxillary strut) may become uneven (either thinned out or too bulky) in various places in the respective dental strut. This bone condition may make the dental restorative process in that particular area more difficult than when such bone loss has not occurred. It could be thought as building a house whose foundation on an unleveled or uneven ground.

In order for the dental prosthetic (or restoration) to be properly fitted to the patient in a substantially esthetically and functionally acceptable position, the dental health care professional (e.g. dental surgeon) may first have to alter the bone of the dental surgical site (especially in those situations where the dental prosthetic is redressing significant tooth loss). This corrective process could start by making one or more incisions in gum area that otherwise designates the dental surgical or restoration site. These incisions substantially allow the gum tissue to be peeled back to expose the bone at the dental surgical site. The dental surgeon, in order to generally make dental surgical site/dental arch symmetrical in all relevant dimensions for the dental restoration (e.g., removable denture) or implant sites (e.g. fixed prosthetics) may then apply one or more cutting tools to generally reduce or remove unwanted high points or thickened places on the exposed bone structure. In other instances, the dental surgeon may add bone material to the exposed bone structure to further fill out the arch's profile or otherwise strengthen its structure.

During this process, the dental surgeon could bring the top portion of the alveolar ridge (e.g., one of the two jaw ridges either on the roof of the mouth or the bottom of the mouth that contain the sockets or alveoli of the teeth) to the correct surgical dimensions ("leveling out") by utilizing a bone foundation guide generally placed upon and secured to the bone structure to substantially guide the cutting/augmenting of the exposed bone. The bone foundation guide solves the problem of "estimating" the vertical height and width of the bone at the "coronal" level by guiding the surgeon's operation of the cutting tools and/or augmentation of the bone. This allows subsequent and accurate placement of the dental implants and respective prosthetics at the proper patient-specific vertical and horizontal levels. This bone adjustment process may also provide for the creation of the proper inter-occlusal room (e.g., the space that exists between the opposing teeth and the open tissue (e.g., that will receive the dental prosthetic) to generally insure that proper jaw operation and alignment, smile line and phonetics occur when the final dental prosthetic is finally located within the patient's mouth.

After the exposed bone has been properly been prepared (e.g., reduced or augmented), the bone foundation guide may be removed. A dental implant surgical guide may be subsequently fitted and attached in its place at the remodeled bone of dental surgical site. The dental implant surgical guide may be used to guide the operation of implant accessories needed to prepare the dental surgical site to receive the dental implants. The dental implant surgical guide may then be used to suitably locate the dental implants into the prepared bone structure. After the dental implants are properly located, the dental implant surgical guide may be removed and healing abutments (if required) may be fitted to the dental implants to create a space in the reattached gum proximate to the dental implant(s) that receives a portion (e.g., the base) of prosthetic or prosthesis (e.g., artificial tooth). Once the healing abutments are attached, the gum tissue may sutured back up and around the dental implant-healing abutment combination.

As needed, a full upper or full lower denture/tooth may be fitted to the implants either at the close of the dental surgery or later after healing of the tissues/osseo-integration of bone to implant(s) has occurred. Once the healing/osseo-integration has finalized, the dental surgeon could remove the healing abutments to open up the space proximate to the implants that receives the base of the prosthetic to place and affix the dental prosthetic securely to the implant(s).

The bone foundation guide and the implant dental surgical guide for the implants are generally considered separate instruments that are generally designed, manufactured and used independently of one another other. The design and creation of these guides can be now be accomplished through digital dentistry (e.g., pre-surgical digital methods and associated apparatuses to obtain and merge medical imaging information taken from the patient's mouth and/or dental castings of the patient's mouth to create a patient-specific virtual models of the preoperative and post-operative mouth and a surgical plan connecting the two models) or manually by dental art and hand (e.g., analogue dental design and preparation).

This separation or compartmentalization of dental guide capabilities could result in higher costs, manpower, and surgical time that could be found than if the two dental guides could be combined into one multipurpose device. The use of such a combination dental appliance could accordingly lead to an increase in the affordability of such dental procedures and results.

Another issue that may arise in such dental implant surgeries is when the dental healthcare professionals locate and affix the bone foundation guide physically upon the dental surgical site (e.g., a portion of bone.) Generally, the dental healthcare professional has to juggle both tasks of locating and affixing (e.g., drilling into the bone for fasteners, then using fasteners to secure the bone foundation guide onto bone) at the same time. The dental healthcare professional in having juggling both tasks may not properly locate the bone foundation guide in desired area of the dental surgical site; may not properly secure the bone foundation guide in place or both.

What could be needed is the present invention namely a bone foundation guide system substantially comprising of a combination of a bone foundation guide used to modify bone structure from a dental implant site (e.g., removing bone with a saw from the bone portion of the dental surgical site; adding bone or a bone analogue to the bone portion of the dental surgical site or both) and further supporting in a stackable manner a dental implant surgical guide (e.g., for generally locating implants to the dental surgical site) and alternatively to the dental implant surgical guide a tissue spacing gasket (e.g., for properly locating a prosthesis relative to the bone foundation guide.)

In one embodiment, a dental implant surgical guide be could removably attached to the bone foundation guide in situ (e.g., after the bone foundation guide has been used to modify a bone structure.) Substantially using the bone foundation guide as a base, the dental surgical implant guide could be used to generally position and locate the implant components (e.g., drill, reamers, abutments, implant drivers, etc.), dental implant or alike into the bone portion of the dental surgical site. Once the implant(s) are properly placed at the dental surgical site, the dental implant surgical guide could be removed from the bone foundation guide and be alternatively replaced with the tissue spacing gasket. In one possible embodiment, the tissue spacing gasket could be located between the bone foundation guide and a prosthesis to at least provide a basic approximation of gum tissue thickness for the gum that would normally cover that area of the dental surgical site to substantially allow for proper adjustment of prosthesis attachment to the implants and alike.

In one possible embodiment, the bone foundation guide could comprise of a body and one or more removable anchoring struts that reversibly connect buccal and lingual walls of the body, an apex of the anchoring strut could denote one or more indentations whose contours matching up with one or more portions of dentition, tissue or both from an opposing alveolar ridge (e.g., the alveolar ridge that is generally located opposite of the alveolar ridge that is hosting the dental implant site) to allow the indentations to removably receive the one or more portions of dentition, tissue or both from an opposing alveolar ridge. In this manner, the patient can then press the patient's at least the one or more portions of dentition, tissue or both of an opposing alveolar ridge upon at least one of the one or more the anchoring struts removably applied to the body to initially hold the bone foundation guide in place upon the dental surgical site. The patient's action could free the attending dental healthcare professional from having to hold the bone foundation guide in place and substantially allow the said professional to use both hands to secure the bone foundation guide in place with fasteners.

Another possible embodiment could further comprise a bone foundation guide prosthesis that is combined with a bone foundation guide. The formed combination could be placed upon the exposed bone segment of the dental implant surgical site and accommodates that portion of the exposed bone segment that is to be subsequently removed during the implant surgery. The patient could bite down upon the combination to bring the opposing first alveolar ridge into contact with the combination. By observing the resulting bite, it can be determined whether or not the bone foundation guide is properly positioned upon the exposed bone segment. This observation could take into consideration several parameters such as telemetry, positioning orientation and aesthetics of the bite. The combination could further allow a direct observation of the fit between the combination and the exposed bone segment.

In this manner, an in situ the bone foundation guide prosthesis interaction with the opposing alveolar ridge relative to the dental implant surgical site prior to any irreversible bone removal from the dental implant surgical site. If proper bite alignment and alike does not exist then combination can be removed from the bone segment; gum tissue at the dental implant surgical site can be re-sutured and the implant surgery can be postponed to allow for proper adjustments to be made as necessary to correct the deviations or other imperfections that caused the bite misalignment and alike.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide an dental implant surgical guide that removably combines with a bone foundation guide to properly place a dental implant-retained prosthesis to a dental surgical site in a manner that reduces patient stress and bruising that may occur than if the two guides were applied separately;

the ability to use a digital virtual model of patent mouth to design a bone foundation guide wherein both the bone foundation guide and a dental implant surgical guide can be conjoined in situ properly locate a one or more dental implants that could be used to locate and secure a fixed dental prosthetic;

to provide a bone foundation guide and dental implant surgical guide that can be combined together to substantially reduce cost, time and man-hours needed in a dental implant surgical procedure to properly locate and attach a dental prosthetic to a dental surgical site;

the ability to use digital dentistry to control the design and manufacture of a dental implant surgical guide-bone foundation guide combination in a manner that digitally controls and refines the accuracy of the resulting bone foundation guide; dental implant surgical guide and a final fixed prosthetic; and to provide a bone foundation guide that is used in conjunction with a tissue spacing gasket, the tissue spacing gasket being used to help properly locate the placement of a prosthesis relative to the placed dental implant(s) by generally taking into account the height (or depth) of gum tissue that could normally cover the exposed bone at the dental implant surgical site;

the ability to design and manufacture a bone foundation guide system wherein a dental implant surgical guide or a tissue spacing gasket that could alternatively could mate and interlock with the bone foundation to generally allow implant components, dental implant or both to pass through the assembled combination onto the bone at a dental surgical guide;

to provide a dental surgical implant guide, bone foundation guide, and tissue spacing gasket to have matching contours and aligned openings and apertures that allow guides and gasket to be assembled into combinations to properly locate and attach a fixed prosthetic to an implant at a dental surgical site;

to provide one or more anchoring struts that could removably and temporarily attach to the front and back of the base of a bone foundation guide, each anchoring strut at a respective apex further define one or more indentations can reversibly receive one or more portions of the tissue, dentition or both of an alveolar ridge that is located opposite of an alveolar ridge that is supporting the dental surgical site;

the ability to have the patient bring one or more portions of the dentition, gum tissue or alike of an alveolar ridge into contact with the anchoring struts to hold the bone foundation guide in place upon the dental surgical site located on the opposing alveolar ridge;

to provide anchoring struts that can be removed from the bone foundation guide after the bone foundation guide has been secured to the dental surgical site by fasteners;

the ability to have the patient temporarily hold the bone foundation guide in place upon the dental surgical site so as to free the dental health care professional from holding the bone foundation guide in place and being able to concentrate instead on securing the bone foundation guide to the dental surgical site with one or more fasteners;

to provide a bone foundation guide and a bone foundation guide prosthesis combination that can interact with both an opposing alveolar ridge and the dental implant surgical site prior to removal of any bone from the dental implant surgical site to substantially provide a proper fit of the bone foundation guide to the dental implant surgical site;

the ability to generally check the bone segment portion that is to be removed from the dental implant surgical site prior to the bone segment portion actually being removed from the dental implant surgical site;

the ability to substantially check the telemetry, orientation, positioning of a final prosthesis placement prior to removal of any bone from the dental implant surgical site; and provide a bone foundation guide prosthesis that attaches by one or more anchor struts to a bone foundation guide to accommodate a bone segment portion of dental implant surgical site prior to the bone segment portion being removed from the dental implant surgical site.

These and other advantages may be realized by reference to the remaining portions of the specification, claims, and abstract.

Brief Description of One Embodiment of the Present Invention

One possible embodiment of the invention could be a bone foundation guide system comprising a bone foundation guide comprising a body having a buccal wall and a lingual wall that is continuously connected by a first end and a second end forming an open surgical space connecting a top of the body with a bottom of the body, the bottom is contoured to removably affix the body to a bone segment of a dental implant surgical site, the body being further contoured to guide the cutting a portion of the bone segment from a dental implant surgical site and as well as supporting a dental implant surgical guide; a bone foundation guide prosthesis as an alternative to the dental implant surgical guide, the bone foundation guide prosthesis combines with the body to accommodates the bone segment portion as placed through the body prior to the bone segment portion being removed from the dental implant surgical site.

Yet another embodiment of the invention could be a method of using a bone foundation guide system comprising the following steps providing a bone foundation guide comprising a body having a buccal wall and a lingual wall that is continuously connected by a first end and a second end forming an open surgical space that further connects a top of the body with a bottom of the body, the bottom is further contoured to removably receive at least a portion of a bone segment of a dental implant surgical site, the body further configured to at least removably support a dental implant surgical guide; providing a bone foundation guide prosthesis in alternative to the dental implant surgical guide to removably attach to the body in a manner that accommodates the bone segment portion as placed through the body prior to the bone segment portion being removed from the dental implant surgical site; combining the body with the bone foundation guide prosthesis; and placing the combination upon the bone segment of the dental implant surgical site prior to the removal of any bone from the dental implant surgical site.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
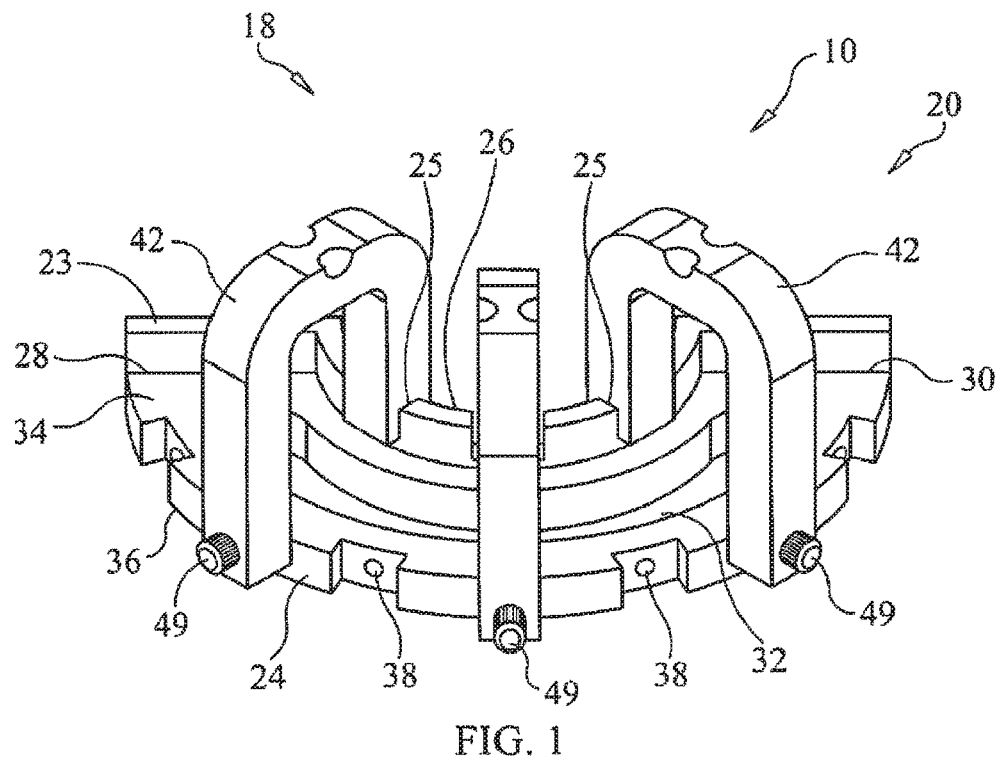
FIG. 1 is substantially a perspective bottom side view of one possible embodiment of the bone foundation guide the invention.
Figure 2:
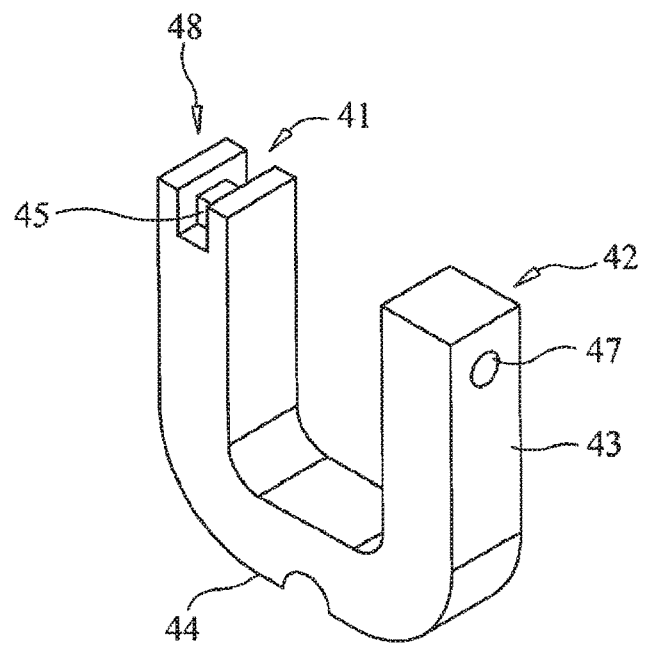
FIG. 2 is a top side perspective view of one possible embodiment of anchoring strut of the present invention.
Figure 3:
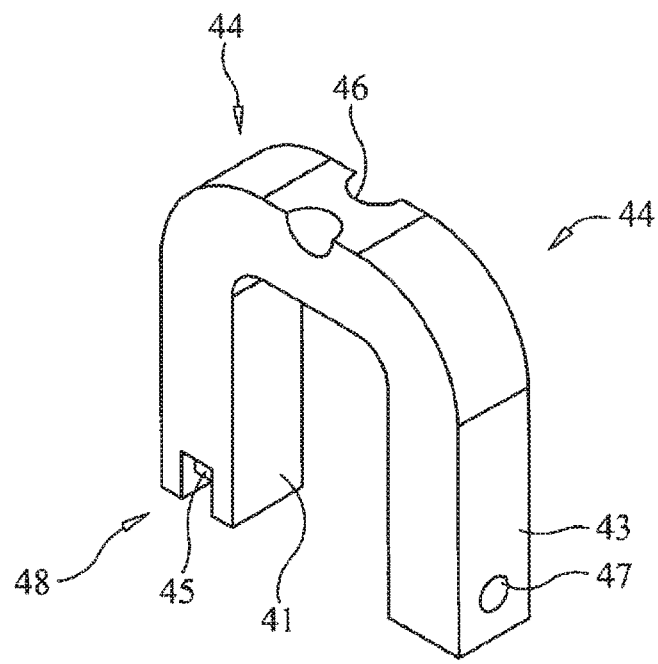
FIG. 3 is a bottom side perspective view of one possible embodiment of anchoring strut of the present invention.
Figure 4:
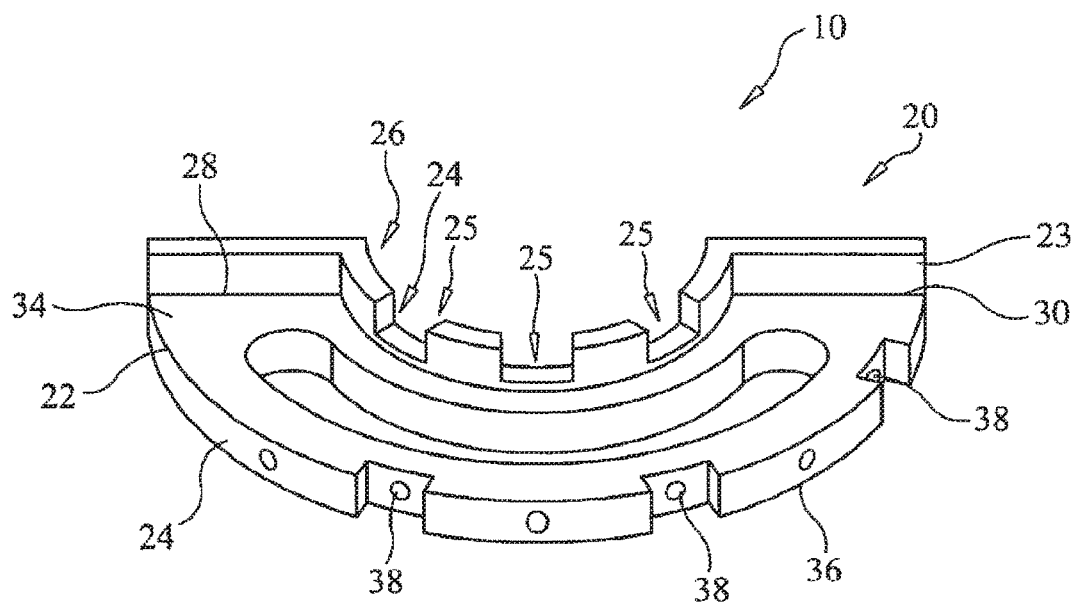
FIG. 4 is substantially a bottom side perspective view of one possible embodiment of the body.
Figure 5:
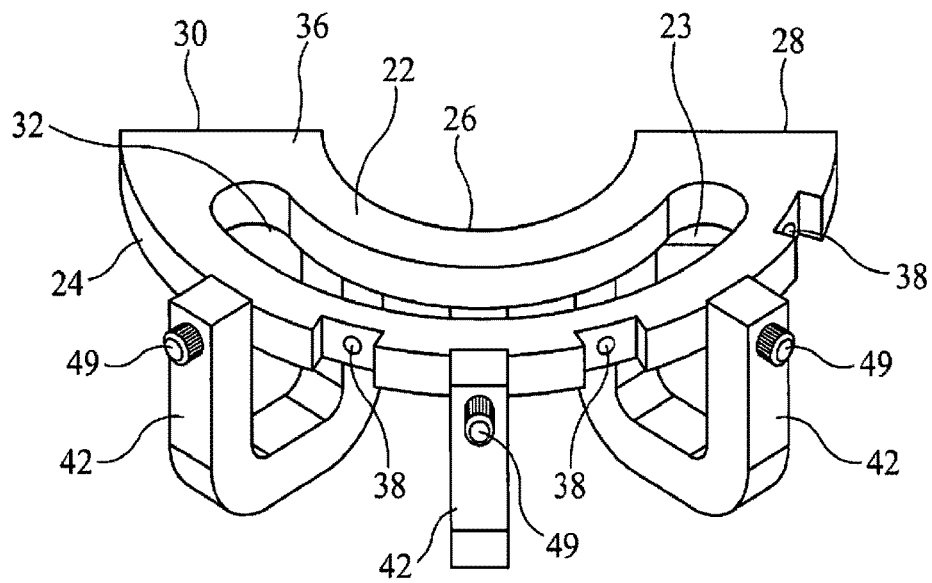
FIG. 5 is substantially a perspective top side view of one embodiment of the bone foundation guide.
Figure 6:
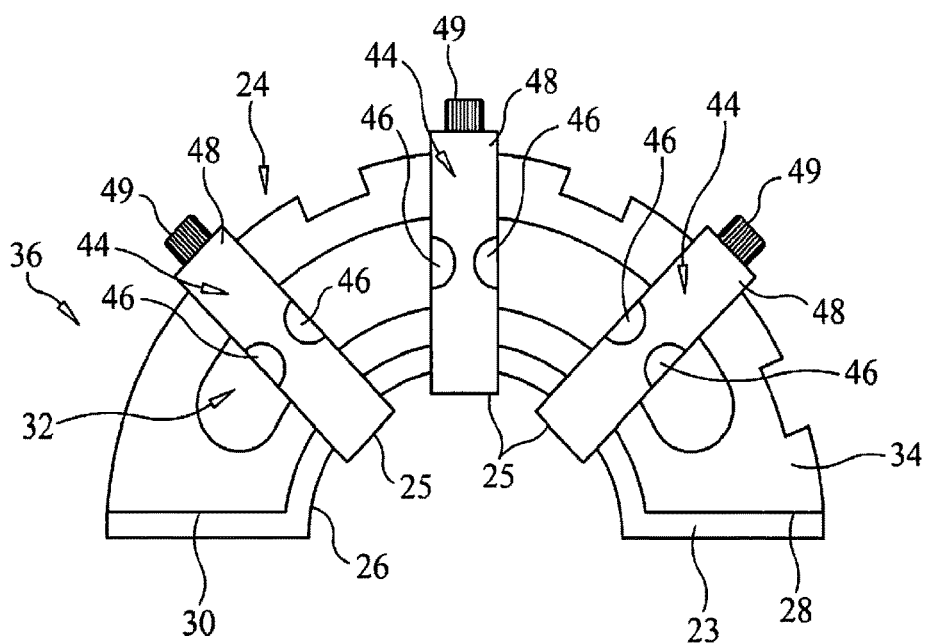
FIG. 6 is substantially a bottom elevation view of one embodiment of the bone foundation guide.
Figure 7:
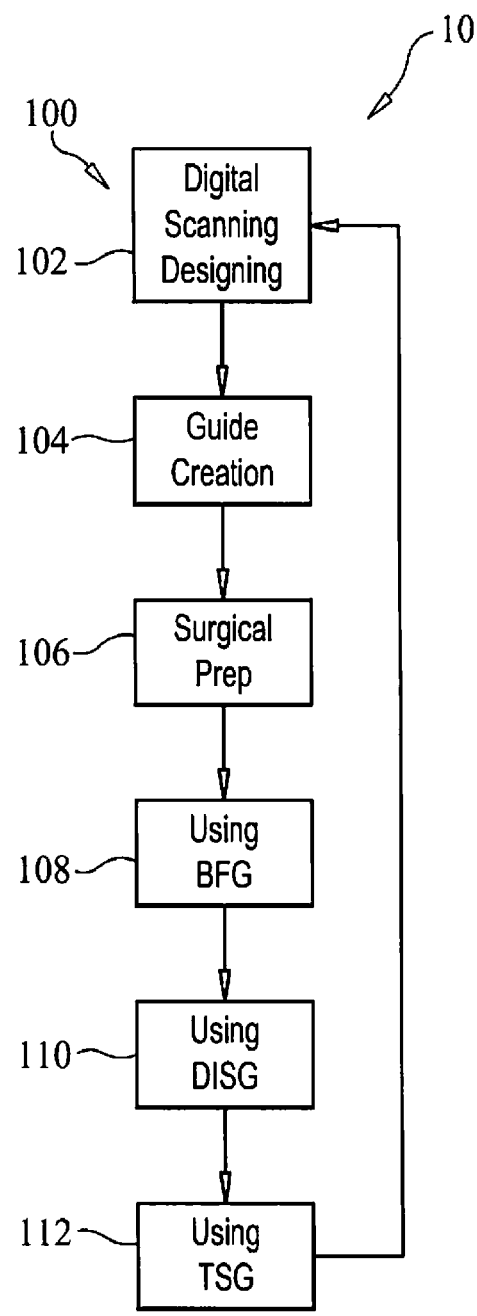
FIG. 7 is substantially a flow chart schematic showing a method of using the invention.
Figure 8:
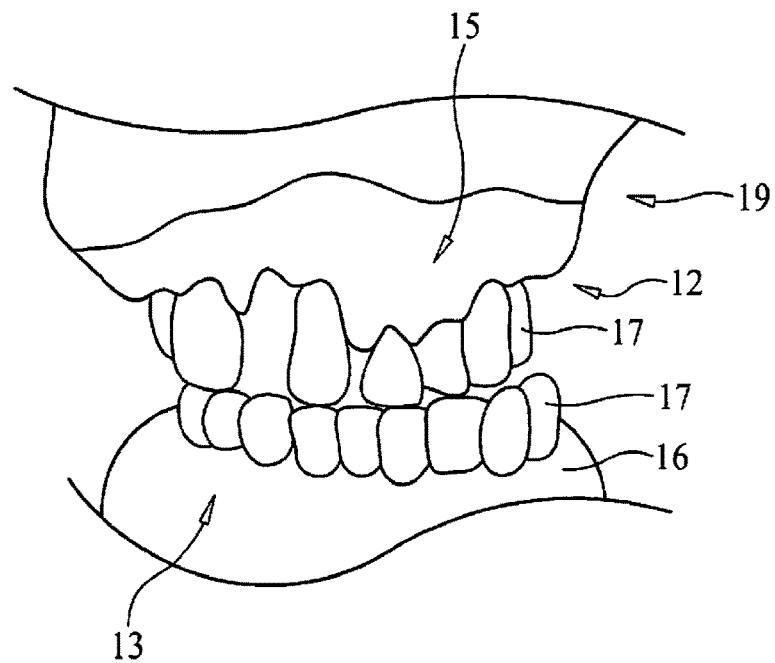
FIG. 8 is substantially an elevation view of patient's mouth showing exposed bone portion of the dental surgical site.
Figure 9:
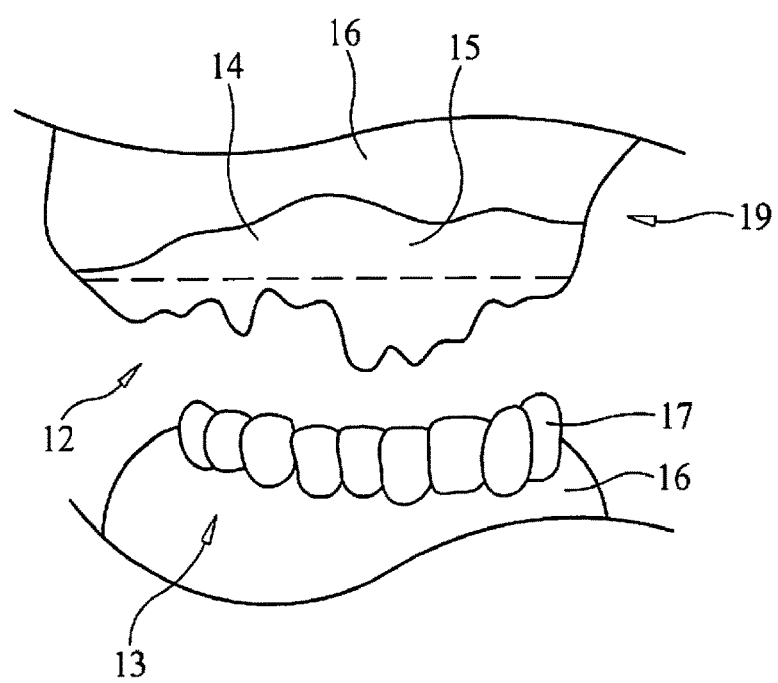
FIG. 9 is substantially an elevation view of patient's mouth showing exposed bone portion of the dental surgical site in an edentulous preoperative state.
Figure 10:
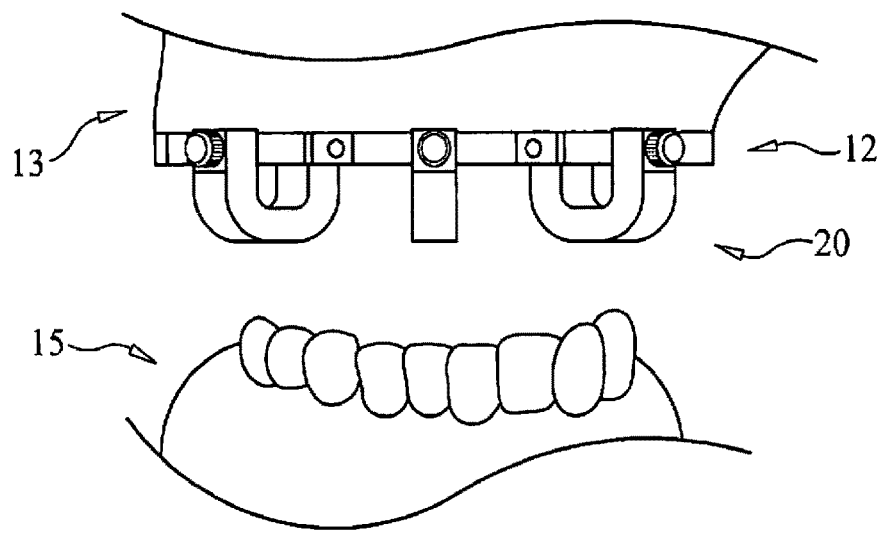
FIG. 10 is substantially a perspective front view of one embodiment of the bone foundation guide with struts being applied to the dental surgical site.
Figure 11:
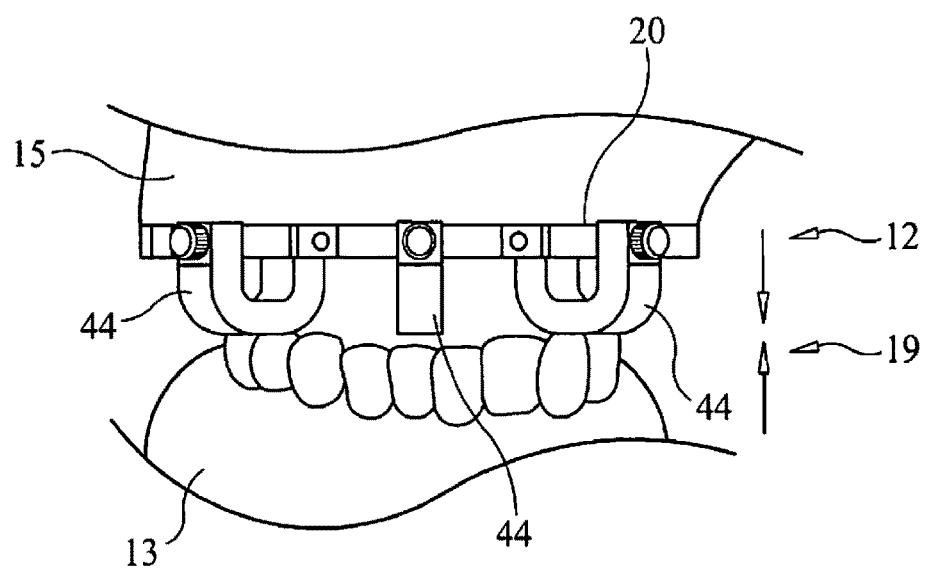
FIG. 11 is substantially a front perspective view of the bone foundation guide with struts being bitten down upon by the patient.
Figure 12:
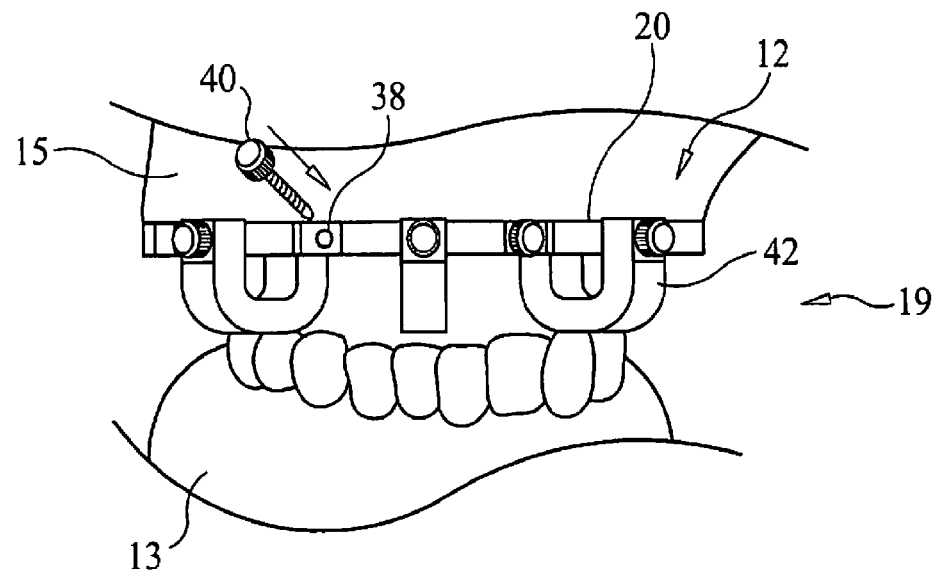
FIG. 12 is a front perspective view of the bone foundation guide with struts with the patient releasing its grip on the bone foundation guide and the strut fasteners being removed.
Figure 17:
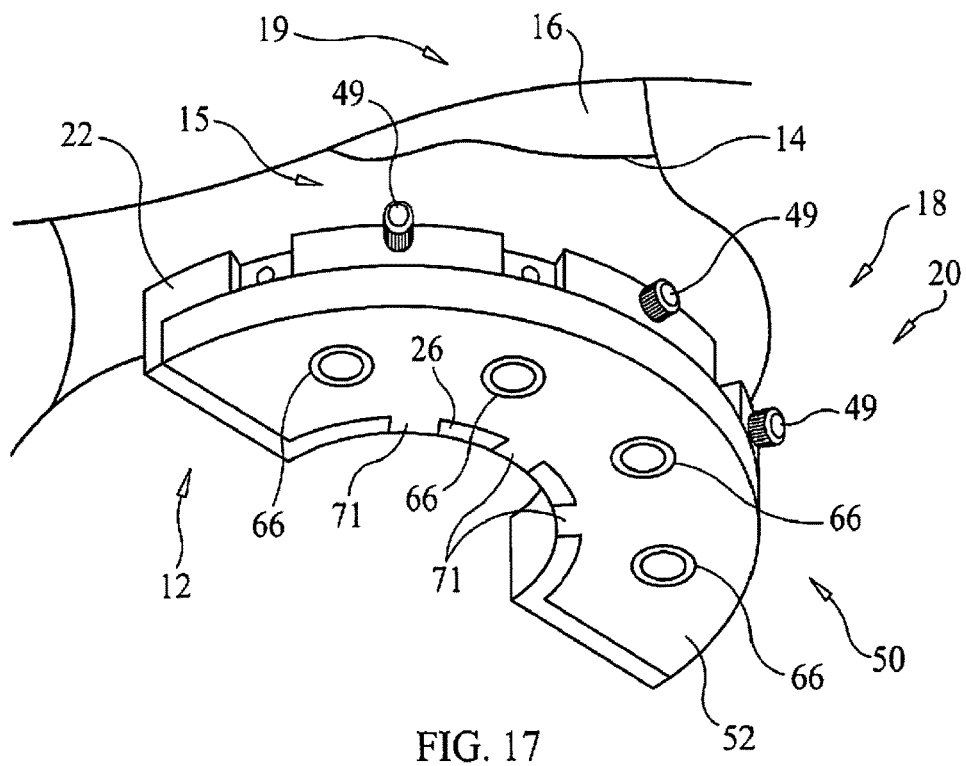
FIG. 17 is substantially an underside perspective view of the combination bone foundation guide and dental implant surgical guide combination.
Figure 18:
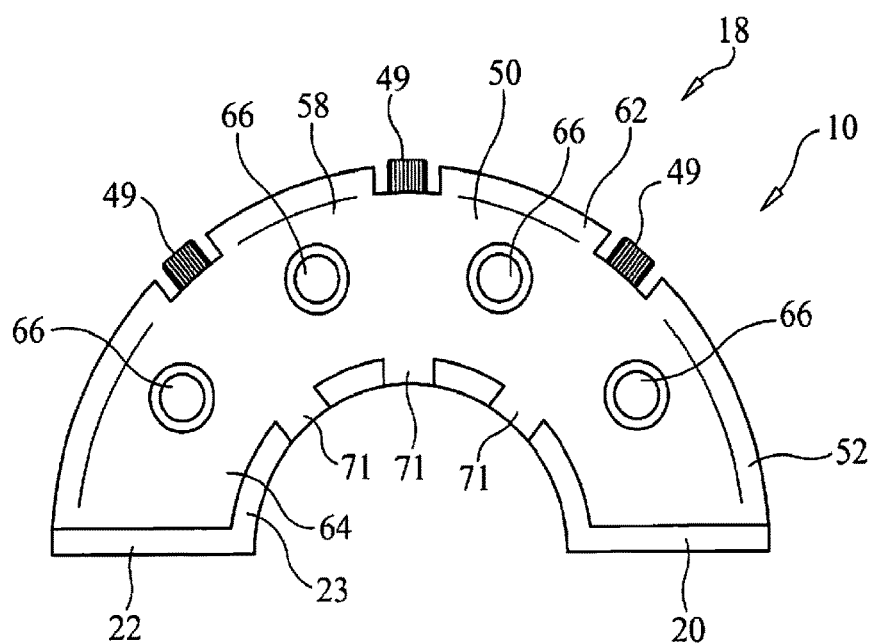
FIG. 18 is substantially an underside elevation view of the combination bone foundation guide and dental implant surgical guide combination.
Figure 19:
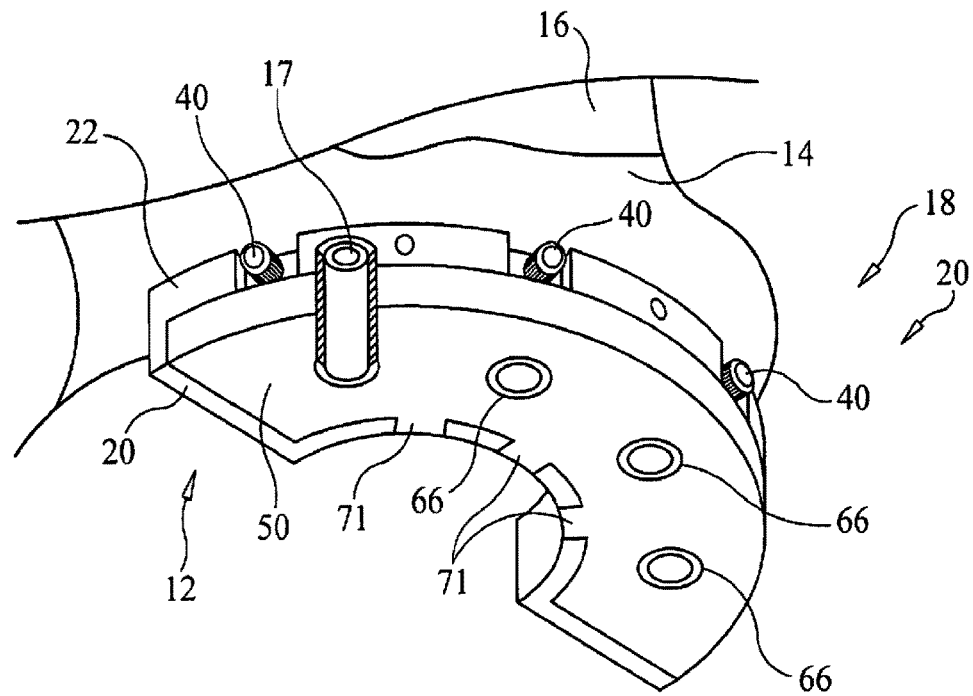
FIG. 19 is substantially a cutaway, perspective view of the combination bone foundation guide and dental implant surgical guide combination.
Figure 20:
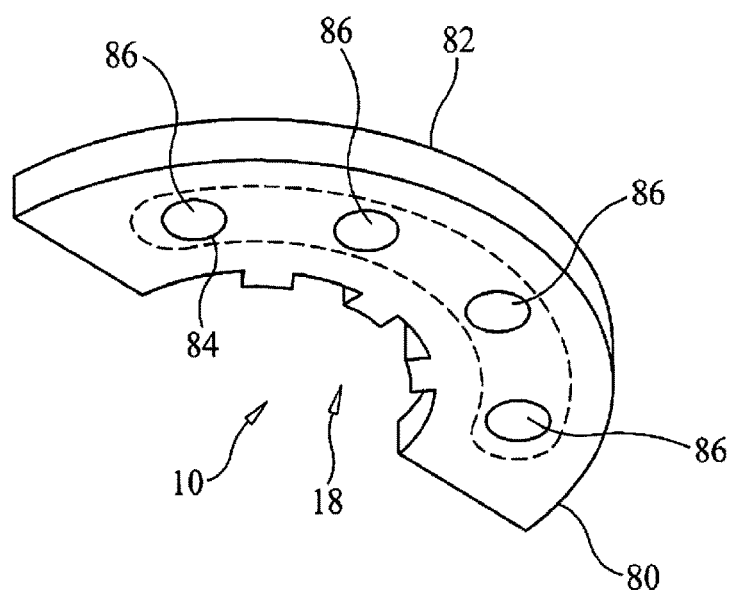
FIG. 20 is substantially a perspective view of the tissue spacer gasket.
Figure 21:
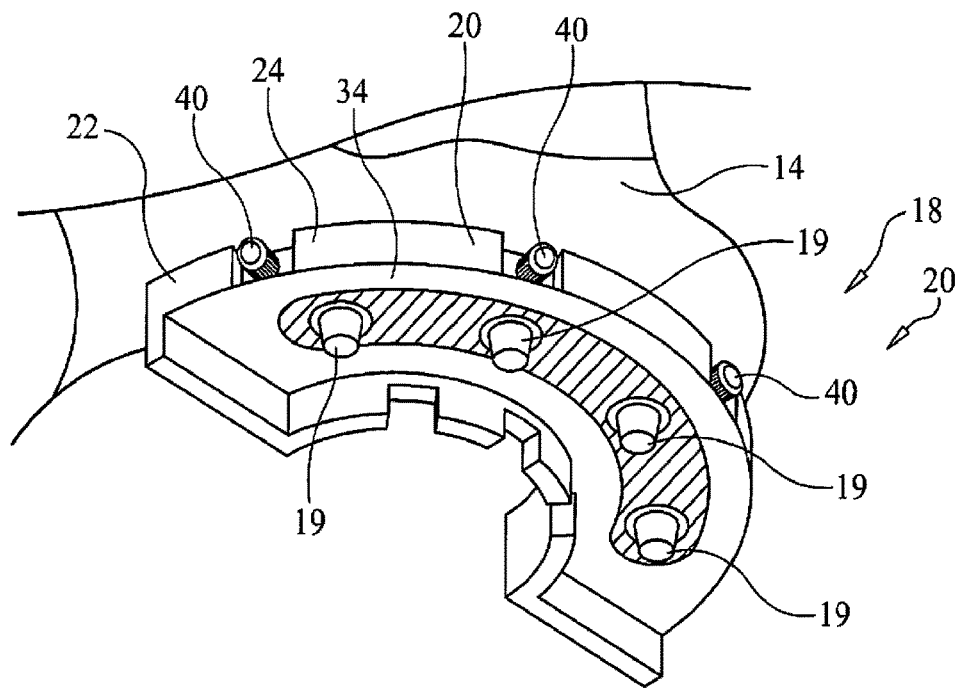
FIG. 21 is substantially a perspective view of the bone foundation guide with abutments attached to the implants.
Figure 22:
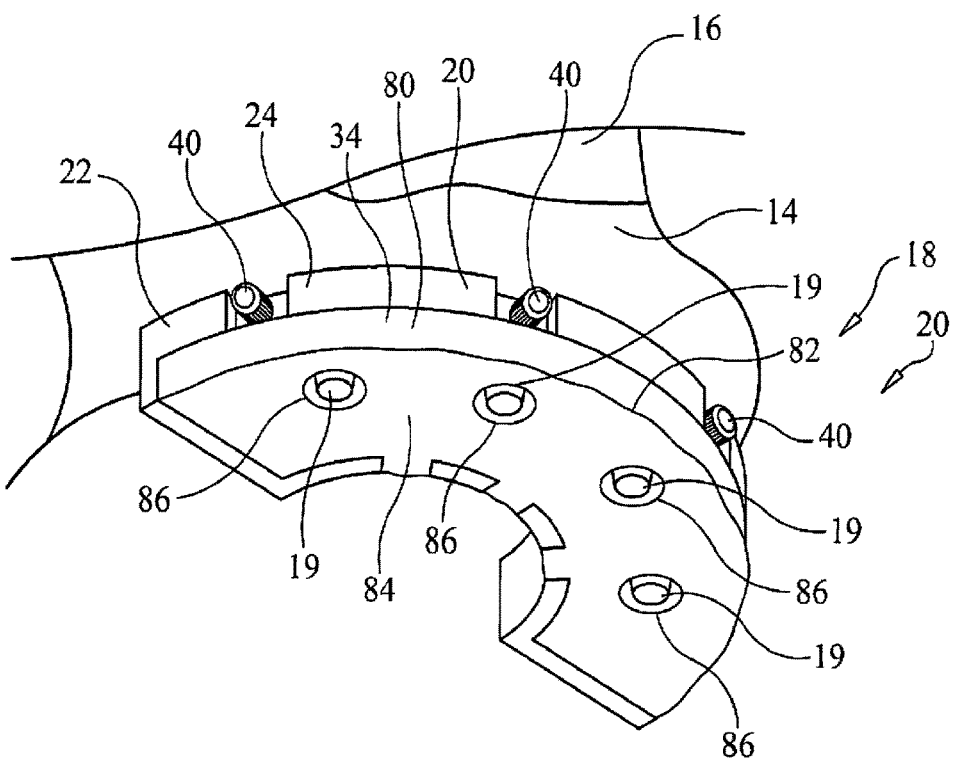
FIG. 22 is substantially a perspective view of the bone foundation guide and tissue gasket combination.
Figure 23:
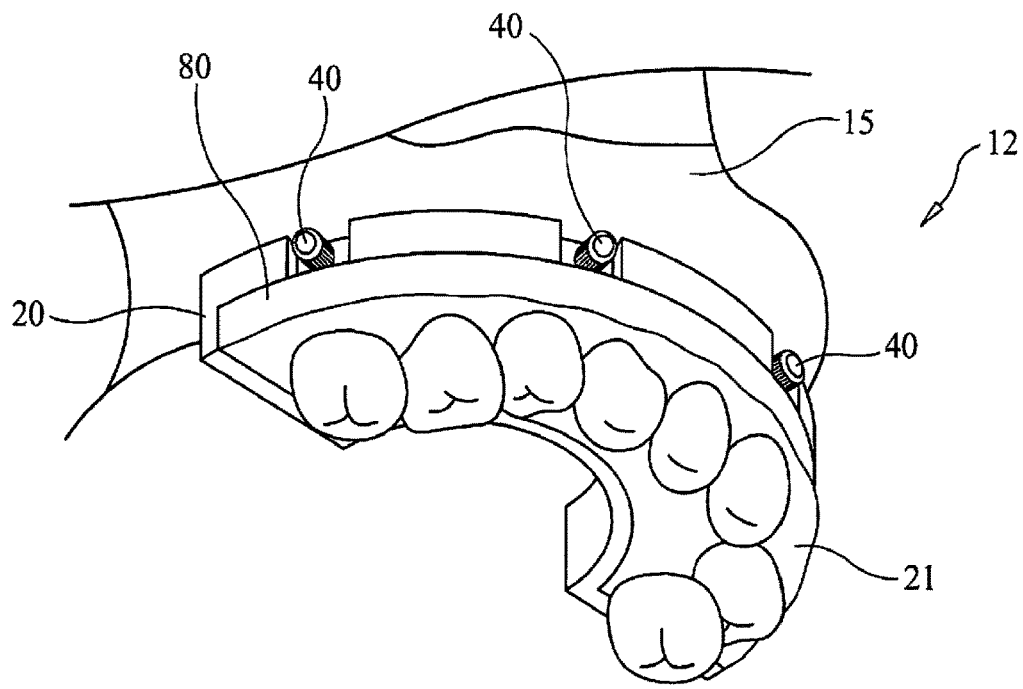
FIG. 23 is substantially a perspective view of the prosthesis applied to the bone foundation guide and tissue gasket combination.
Figure 24:
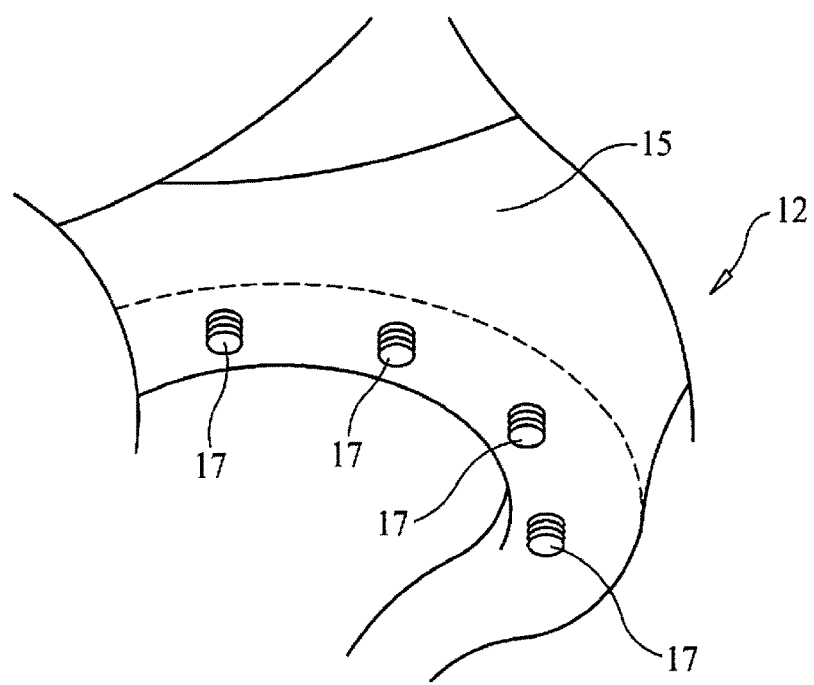
FIG. 24 is substantially a perspective view of the dental surgical site with the bone foundation guide, tissue gasket and prosthesis removed.
Figure 25:
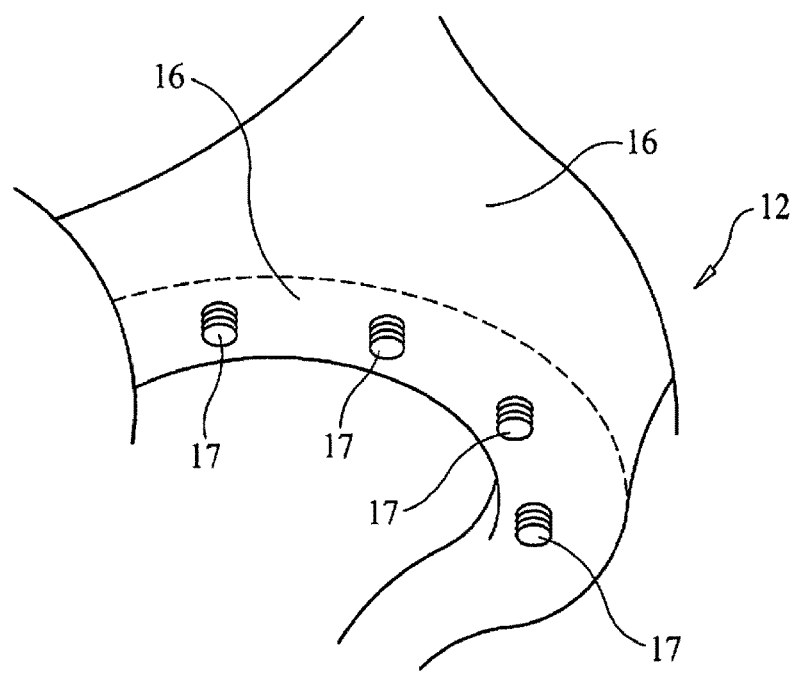
FIG. 25 is substantially a perspective view of the dental surgical site with the bone foundation guide, tissue gasket and prosthesis removed and gum tissue sutured back into place at the dental surgical site.
Figure 26:
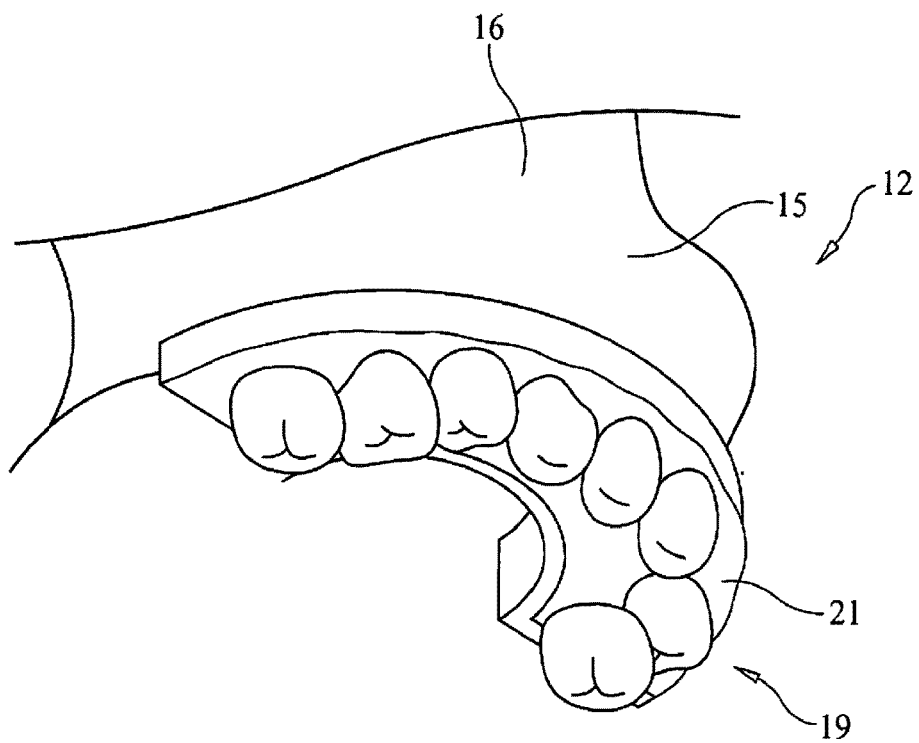
FIG. 26 is substantially a perspective view of the dental surgical site with gum tissue sutured back into place and prosthesis relocated upon the implants.

The present invention 10 could be a bone foundation guide system 18 and method or process 100. As substantially shown in FIGS. 1, 17, and 19 the bone foundation guide system 18 could comprise a bone foundation guide 20, a dental implant surgical guide 50 and in at least one embodiment, a tissue spacing gasket 80 as well. The bone foundation guide body 22, the dental implant surgical guide 50 and tissue spacing gasket 80 may be designed and created together through digital dentistry in which scans of the patient's mouth 35 (along with impressions and castings thereof) may be used to create a virtual model (not shown) of the patient's existing mouth; to develop a virtual model of the patient's mouth both pre-dental and post-dental surgery; and to develop a dental surgical plan that connects the two patient-specific virtual models. In this manner, the dental surgical planning can provide for the manufacture the bone foundation guide 20, dental implant surgical guide 50 and tissue spacing gasket 80 so that the contours of the bone foundation guide body 22 may be created to fit upon the exposed bone 14 of the dental surgical site 12. Further, the dental implant surgical guide 50 contours may also match those of the dental implant surgical guide 50 and the tissue spacing gasket 80 to enable dental implant surgical guide 50 and the tissue spacing gasket 80 to alternately be removably attached to and be supported by the bone foundation guide 20.

As substantially shown in FIGS. 1, 2, 3, 4, 5 and 6 the bone foundation guide 20, as substantially used by a dental healthcare professional such as a dental surgeon (not shown) to substantially modify (e.g., reduce, augment or both) the bone 14 of the dental surgical site 12 as needed for a successful dental surgery. The bone foundation guide 20 could comprise a bone foundation guide body 22 with a buccal wall 24 and lingual wall 26 connected together at their respective ends by a first end 28 and a second end 30. The first end 28 and the second end 30 could be holding the buccal and lingual walls 24, 26 apart from one and other in a substantially parallel fashion to generally create and define an open surgical space 32 (e.g., that generally passes through the bone foundation guide body 22) to generally continuously connect a portion of the top 34 of the body 22 with a portion of the bottom 36 of the body 22.

Figure 13:
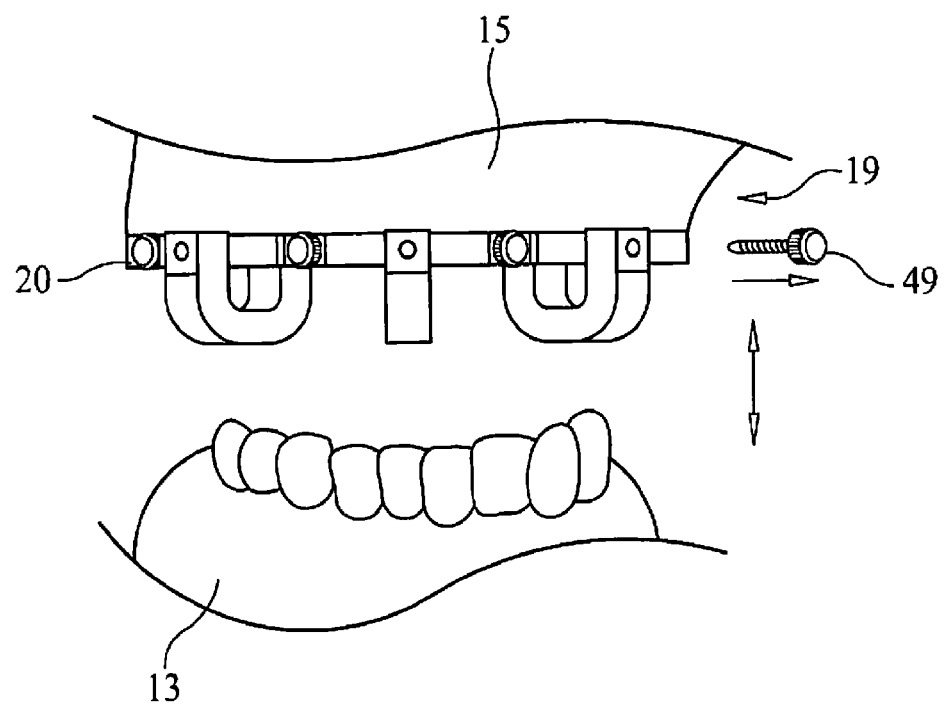
FIG. 13 is substantially a front perspective view of the bone foundation guide with struts, the strut fasteners being removed from the respective strut.
Figure 14:
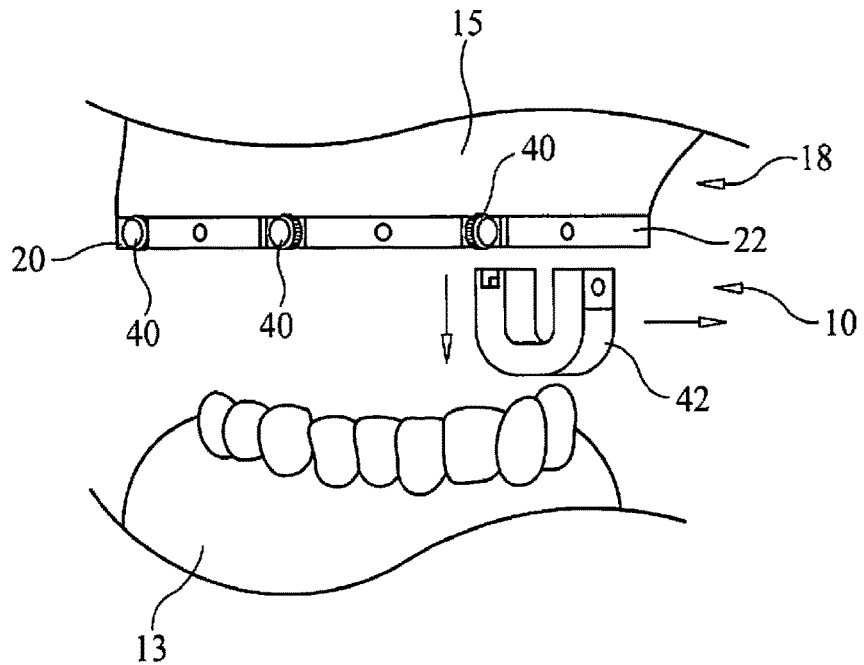
FIG. 14 is substantially a front perspective view of the bone foundation guide with struts, the strut being removed the bone foundation guide body.
Figure 15:
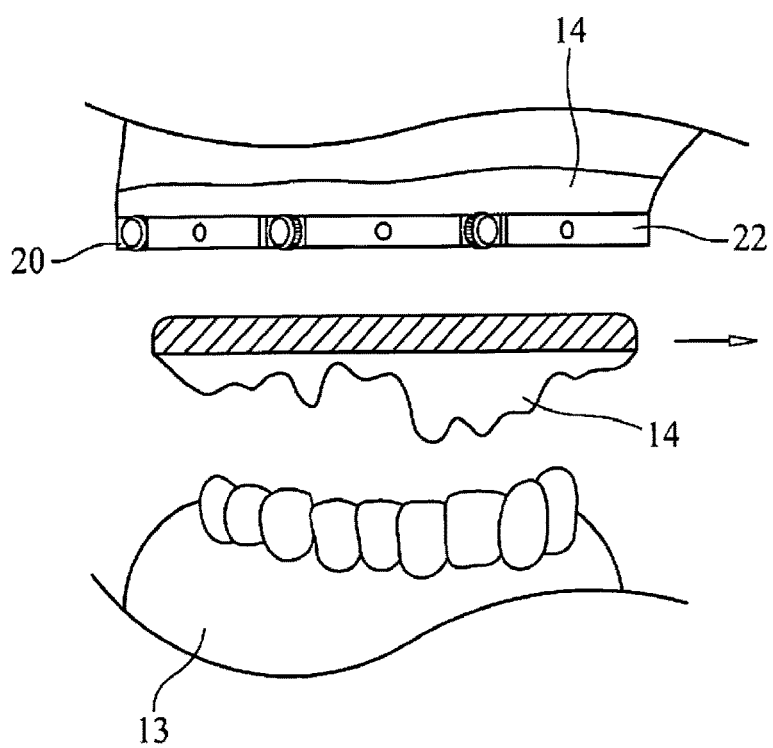
FIG. 15 is substantially a front perspective view of the bone foundation guide with struts removed and the harvested bone being removed from the dental surgical site.
Figure 15A:
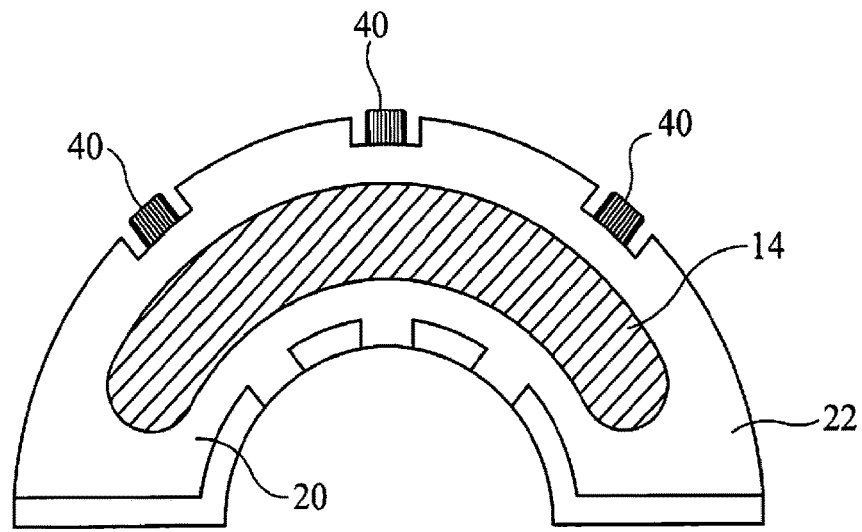
FIG. 15A is substantially a bottom elevation view of the bone foundation guide with struts and the harvested bone removed from the dental surgical site.
Figure 16:
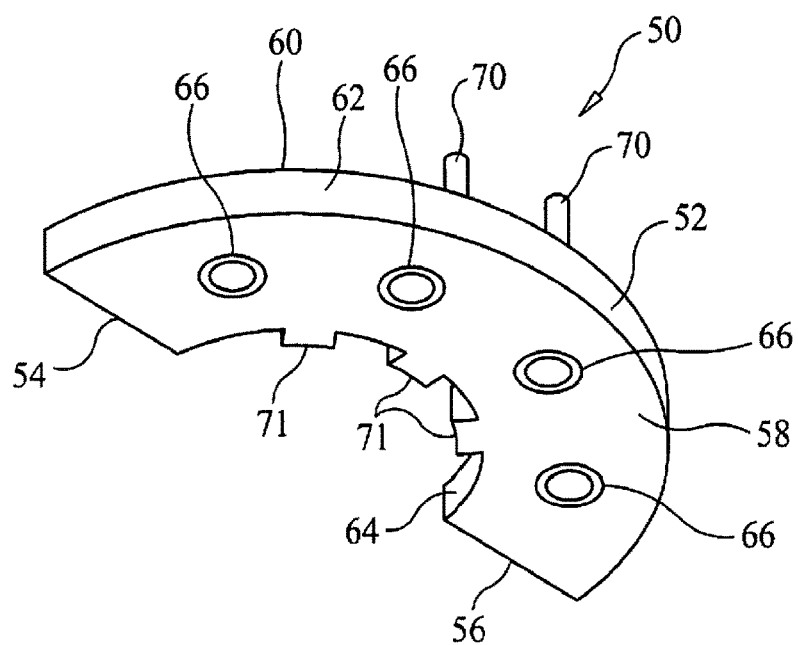
FIG. 16 is substantially an underside elevation view of the bone foundation guide with struts removed and the harvested bone removed from the dental surgical site

The bone foundation guide body 22 may be further penetrated by one or more attachment apertures 38 that may be oriented to pass through a buccal 24 wall. Body fasteners 40 may pass through the attachment apertures 38 to into the bone 14 of the dental surgical site 12 to removably secure the bone foundation guide body 22 to dental surgical site 12. (Substantially shown in FIG. 13.) The attachment aperture 38 could further feature a reinforcement collar (not shown) to support and guide the fastener 40 through the attachment aperture 38. In other embodiments, the attachment apertures 38 could pass though the body 22 connecting top 34 and bottom 36 or through the lingual wall 26 to provide body attachment to the dental surgical site 12. The body may further have a cutting guard 23 extending up from the top of the lingual wall 26 to prevent a cutting implement (not shown) when used with the bone foundation guide in removing bone 14 from a dental surgical site from unwantedly cutting the tongue or other portions of the patient's mouth 19. This cutting guard 23 may further feature out or more cutouts 25 that may be used to anchor and align other portions.

Some embodiments of the bone foundation guide body 22 may further comprise one or more anchoring struts 42 that may be removably attached to the buccal wall 24 and the lingual wall 26 between the first end 28 and the second end 30. The anchoring strut 42 may have at its outer apex 44 one or more indentations 46 that can match one or more portions of gum, dentition or both the patient's first or opposing alveolar ridge 13 (e.g., the opposing alveolar ridge 13 is located opposite of or opposing to the second alveolar ridge 15 that is supporting the dental surgical site 12. Meaning if the dental surgical site 12 is on the upper alveolar ridge then the opposing alveolar ridge 13 could be the lower alveolar ridge.) The front end 43 of anchoring struts 42 may be penetrated by strut apertures 47 that allow strut fasteners 49 (e.g., tapered pins) to penetrate through the anchoring strut 42 to the buccal wall 24. The strut fasteners 49 may removably attach to the anchoring strut 42 by the buccal wall 24 and be held in place by frictional force. The other or rear end 41 of the anchoring strut 42 may have a strut groove 48 that fits over a respective cutout 25. A tab 45 within the strut groove 48 may be removably received within the respective cutout 25 to further reversibly attach the rear end 41 to the cutting guard 23.

The anchoring strut 42 may allow the patient itself press at least a portion of gum tissue, dentition or both of the opposing alveolar ridge 13 upon at least one anchoring strut 42 of the bone foundation guide 20 to generally hold the bone foundation guide 20 in place upon the dental surgical site 12 (e.g., the exposed bone.) In particular, that portion of gum tissue, dentition or both of the opposing alveolar ridge 13 could be received with the indentation(s) 46. The patient's action (e.g., substantially clamping down with patient's mouth upon the bone foundation guide 20 in situ could allow the patient to temporarily and removably hold the bone foundation dental upon the dental surgical site while the dental health care professional (not shown) is free to use both hands to attach the bone foundation guide 20 in place with body fasteners. Once the bone foundation guide 201 is secured by body fasteners 40 to the bone portion of the dental implant surgical site 12, the patient could remove one or more portions of the opposing alveolar ridge 13 from the one or more indentations 46 upon the one or more anchoring struts 42 (e.g., the patient opens its mouth to stop biting upon the anchoring struts 42.) The dental health care professional can then proceed with the removal of the strut fasteners 49 from the bone foundation guide 20 so as to be able to lift the anchoring struts 46 free and clear from the body 22.

The use of anchoring struts 42 can also be applied to bone reduction guides that lack the present inventions ability to combine or stack together with the dental implant surgical guide or tissue spacing gasket. In such instances, bone reduction guides are not contoured to accept the dental implant surgical guide or tissue spacing gasket but could have a body to which the anchoring struts 42 are applied to allow the patient to substantially clamping down with patient's mouth upon the bone reduction guide in situ could allow the patient to temporarily and removably hold the bone reduction guide upon the dental surgical site. The portions of dentition, teeth or both of the opposing alveolar ridge could be received with the impressions located upon the apex of anchoring struts 42 to hold the bone reduction guide in place while the dental health care professional (not shown) is free to use both hands to attach the bone reduction guide in place with fasteners to the dental surgical site. Once the fasteners have secure the bone reduction guide to the dental surgical site, the patient could release its bite upon the anchoring struts. The dental healthcare professional can then remove the anchoring struts 42 from the body of the bone reduction guide to allow the bone reduction guide to be used to alter bone structure at the dental surgical site.

As substantially shown in FIGS. 16, 17, 18, and 19 once the anchoring strut(s) 42 are removed from the bone foundation guide body 22, the dental implant surgical guide 50 could be removably attached to the top 34 of the body 22. The dental implant surgical guide 50 could be so anchored to dental surgical site 12 to generally allow dental implant surgical guide 50 to be substantially be used to guide and locate the placement of dental implants within dental surgical site 12.

The dental implant surgical guide 50 could comprise a dental surgical guide body 20 having a first end side 52 and second end side 54 that terminates the dental surgical guide body 52 and along with a top side 58 and a bottom side 60 that continuously connect a buccal side 62 with a lingual side 64. The bottom side 60 of the dental implant surgical guide 50 can be digitally designed and manufactured to have a contour that substantially matches and removably accepts the top 34 of the bone foundation guide 20. The top 34 of the bone foundation guide body 22 may also be digitally designed and created to substantially match and to receive the bottom side 60 of the reciprocal dental surgical guide body 52 to allow the conjoining of the two guides 20, 50 in a stackable manner so that the bone foundation guide 20 acts as a base or foundation for the dental implant surgical guide 50.

The dental surgical guide body 52 can be further penetrated by one or more implant apertures 66 that could continuously connect the top side 58 to the bottom side 60 to guide implant preparation and attachment to the dental operation site 12. The dental surgical guide body 52 to removably attach to the body 22 could utilize a wide variety of attachment means. One such possible attachment means could make use one or more guide pins 70 and one or more guide tabs 71 and their frictional interplay with the body 22. The guide pins 70 could protrude out from the bottom side 60 by the buccal wall 62 to be removably received within pin apertures on the top 34 of the body 22 along the buccal wall 24. The one or more guide tabs 71 could extend outwards from the lingual side 64 to be respectively received by the cutouts 25 of the cutting guard 23. The guide tabs 71 and guide pins 70 along with the lingual side 64 matching the contour of the cutting guard 23 could provide a snap-in fit of the dental implant surgical guide 50 to the bone foundation guide 20.

The conjoining or stacking capability of the two guides 20, 50 could alleviate the need to remove the bone foundation guide 20 from the dental surgical site 12 prior to attaching the dental implant surgical guide 50 to the dental surgical site 12 as well as alleviate the need to attach the dental implant surgical guide 50 directly to the dental surgical site 12 and the like. This combining of the two guides 20, 50 could also reduce the time, money, effort, patient discomfort and alike that would otherwise occur if the guides 20, 50 were used separately from one and other. When so combined together, the dental implant surgical guide 50 generally surrounds the bone foundation guide's open surgical space 32 to allow implant components, implants or both to pass through the dental implant surgical guide's implant aperture(s) 66 and on through the of the open surgical space 32.

As substantially shown in FIGS. 20, 21, 22 and 23, one other possible embodiment of the invention 10 could further comprise a tissue spacing gasket 80 that can be alternatively used with the bone foundation guide 50 instead of the dental implant surgical guide 50 or the anchoring strut(s) 42. The tissue spacing gasket 80 could fit between the bottom 36 of the bone foundation guide 20 and the dental surgical site 12 to allow the proper placement of prosthesis 21 upon the placed implants by providing an approximation of the distance or thickness of the gum tissue 16 that otherwise covers the dental surgical site 12. The placement of the tissue spacing gasket 80 upon the bone foundation guide top 34 where the tissue spacing gasket 80 is generally sandwiched between the bone foundation guide 20 and the prosthesis 21 could allow the tissue spacing gasket 80 provide additional benefits besides correcting for thickness of the missing (e.g., peeled back) gum tissue 16. The tissue spacer guide 80 could help cradle the prosthesis and maintain the prosthesis proper vertical and centric positions as the prosthesis is being fixed upon the implants. When the prosthesis 21 is generally fixed about the implants (e.g., to the abutments 17 attached to the implants), dental acrylic could be injected into the prosthesis to secure implant abutments to the prosthesis. The tissue spacing gasket 80 could help block out the undercut of the abutments 17 to generally prevent the acrylic from reaching the undercuts and thus preventing unwanted or premature attachment of the prosthesis to the implants 17. The tissue spacing gasket 80 could further prevent acrylic from reaching and contaminating the exposed bone 14.

The tissue spacing gasket 80 could be made from a pliable polymer that forms a gasket top 84 upon which the prosthesis could rest and to a gasket bottom 82 which is reversibly received by the bone foundation top 34, the gasket top 84 and the gasket bottom 84 being continually connected by one or more gasket apertures 86. The one or more gasket apertures 86 could have the same alignment and size of the implant apertures 66 of the dental implant surgical guide 50. In at least one embedment, the tissue spacing gasket 80 could denote a gasket open surgical space (not shown) that continuously connects gasket top 84 and gasket bottom 82, the gasket open surgical space generally matching the footprint of the bone foundation guide's open surgical space 32.

To generally removably affix the tissue spacing gasket 80 to the bone foundation guide 20, the tissue spacing gasket 80 could have one or more gasket pins that protrude from the gasket bottom 82 and could be removably received within apertures on the bone foundation guide top 34 by the buccal wall 24 that received guide pins 70. The tissue spacing gasket 80 could further have the gasket tabs 88 that could be removably be received within the cutting guard cutouts 25. The tissue spacing gasket tabs 88 could generally match the size, placement and orientation of the dental implant surgical guide's guide tabs 71.

As substantially shown in FIGS. 27-30, another possible embodiment of the invention 10 could further comprise a bone foundation guide prosthesis 200 that can be removably combined with the body 22 of the bone foundation guide to form a bone foundation guide prosthesis-body combination 202. The combination 202 can be applied to the unaltered bone segment 14 of the dental implant surgical site 12 and can further can be used in contact with the first alveolar ridge 13 that is opposing to the dental implant surgical site 12 to check the placement of the bone foundation guide 20 upon bone segment 14 of the dental implant surgical site 12. As the respective patient bites upon the combination, the opposing or first alveolar ridge 13 (e.g., opposing teeth) could be brought into contact with the teeth portion 204 of the bone foundation guide prosthesis 200.) The various parameters (e.g., orientation, telemetry, positioning, aesthetics, and the like) as presented by the opposing alveolar ridge-to-bone foundation guide prosthesis bite 206 could reflect (e.g., generally act as an analogue representation) the final prosthesis-to-opposing first alveolar ridge bite. This bite compression could also ensure solid contact of the combination 202 upon the bone segment 14 of the dental implant surgical site 12 prior to any bone removal by use of the bone foundation guide 20. If the observed parameters or the bone foundation guide-to-bone segment fit show any significant departure or inconstancy with the surgical dental implant plan, the dental implant surgery could be halted prior to any irreversible bone alteration at the dental implant surgical site 12. The combination 202 can then be removed from the dental implant surgical site 12 (e.g., the bone segment 14) and the gum tissue can be re-sutured at the dental implant surgical site 12 to allow greater time to reformulate the associated surgical dental implant plan to take into further consideration those factors that caused the departure or inconsistency in the first place.

Figure 31:
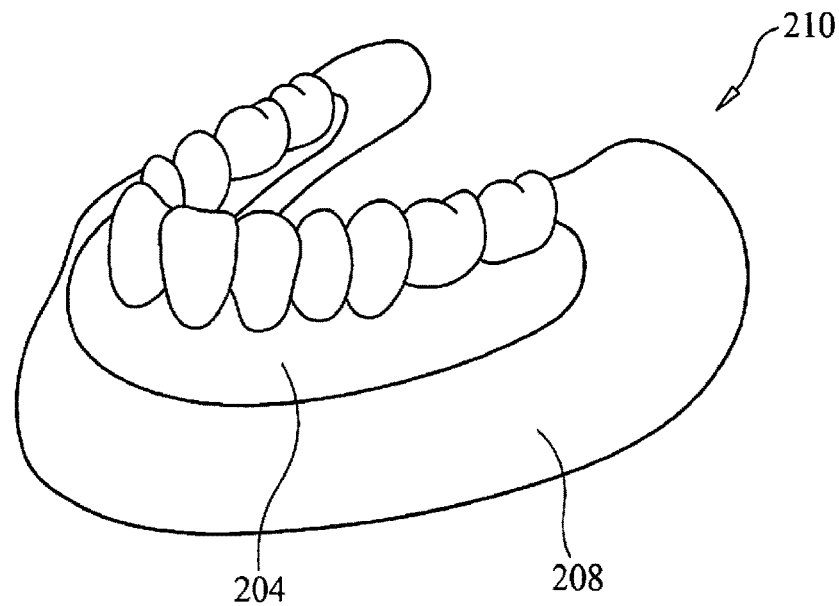
FIG. 31 is substantially a perspective view of the bone foundation guide prosthesis and denture base combined to form a denture.

As substantially shown in FIG. 31, in one possible version once the bone foundation guide prosthesis (or suitable portion thereof) 200 is removed from the body 22, the tooth portion 204 of the multiple piece or non-unitary version of bone foundation guide prosthesis 200 could be further combined with a denture base 208 to form a denture 210. In that cases where the implant surgery was halted due to bite misalignment between the first alveolar ridge (not shown) and the bone foundation guide prosthesis 200, the denture 210 could then be used by the respective patient (not shown) until proper adjustments had been made as necessary to correct the deviations or other imperfections that caused halting of the implant surgery that could allow the dental implant surgery to proceed forward again.

Figure 29:
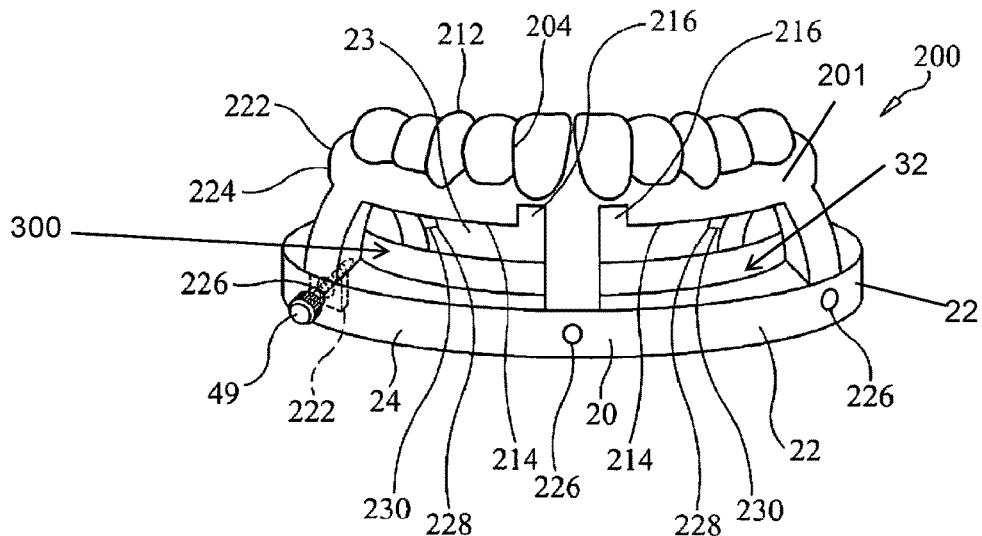
FIG. 29 is substantially a perspective cutaway view of the bone foundation guide prosthesis being combined with the bone foundation guide.
Figure 30:
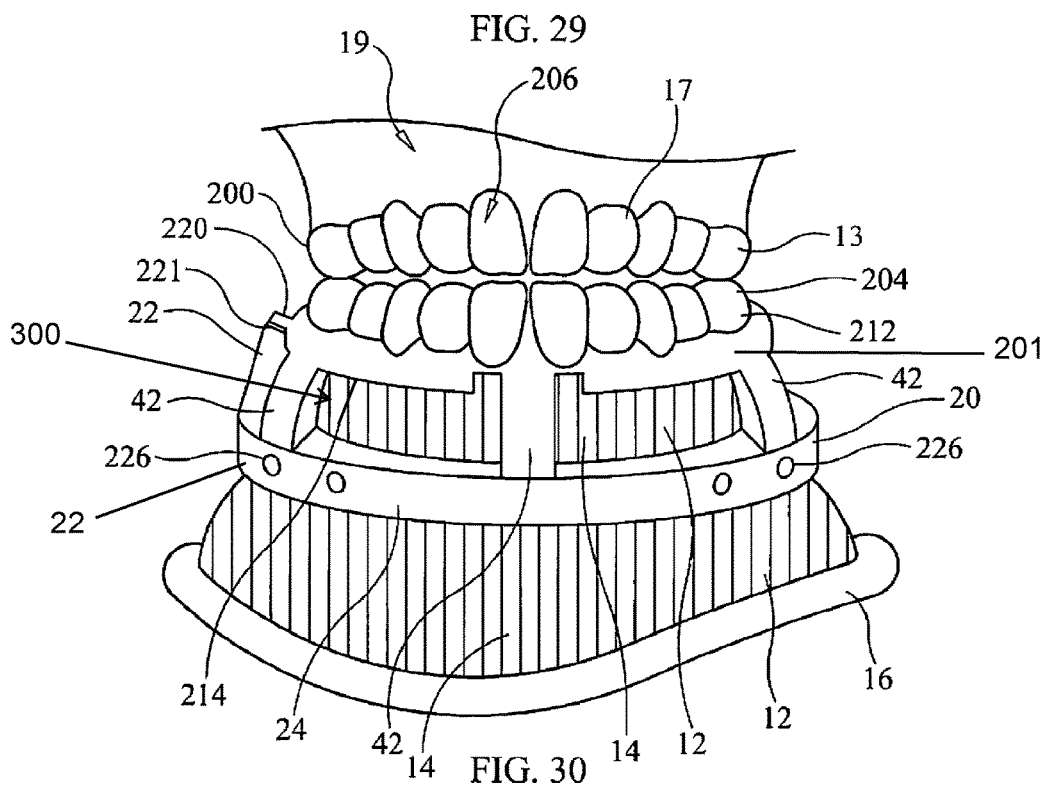
FIG. 30 is substantially a perspective view of opposing alveolar ridge brought into contact with the bone foundation guide prosthesis and the bone foundation guide combination.

The bone foundation guide prosthesis 200 could comprise the teeth portion 204 having a top side 212 substantially replicating the teeth or the bite of the final prosthesis (not shown) and a bottom side 214 that could support one or more anchor struts 42. The bottom side 214 could further define cutouts 216 that allow a visible inspection of the bone segment 14 where the bone segment 14 comes into contact with the bone foundation guide prosthesis 200 (e.g., one or more undersides 215 of the anchor struts 42 could be contoured to receive and contact a portion of the bone segment 14) through a space or gap 300 defined between the body 22 of the bone foundation guide 20 and the body 201 of the bone foundation guide prosthesis 200 as shown in FIGS. 29-30. As shown in FIG. 30, a portion of the bone segment 14 protrudes through the body 22 of the bone foundation guide 20 and into the space or gap 300, such that the space or gap 300 is shown as accommodating the portion of the bone segment 14 that protrudes through the body 22 of the bone foundation guide 20 and into the space or gap 300. As shown in a comparison of FIG. 29 to FIG. 30, this portion of the bone segment 14 that protrudes through the body 22 of the bone foundation guide 20 and into the space or gap 300 passes through the open surgical space 32 of the body 22 of the bone foundation guide 20. In one possible embodiment, the bone guide foundation prosthesis bottom 214 could limit the bone segment contact to three points of contact to substantially prevent rocking of the bone guide foundation prosthesis 200 upon the bone segment 14.

Removable attachment of the struts 42 to the body 22 could assist the attachment of the bone foundation guide prosthesis 200 to the bone foundation guide 20. The bone foundation guide prosthesis 200 could have one or more support tabs 220 proximate to each end of the bone foundation guide prosthesis 200 that could be removably received within corresponding support slots 220 in the lingual wall cutting guard 23. Proximate to the rear end 41 of the anchor strut 48 could feature a securing tab 228 that could removably attached to a corresponding securing slot 230 also formed in the lingual wall cutting guard 23.

At least one anchoring strut 48 could have its front end 43 form an attachment tab 222 that fits into a respective tab slot 224 formed by the body's buccal wall 24 that could be accessed at the top 34. Both the attachment tabs 222 and their respective attachment slots 224 could be suitably angled to assist the attachment and removal of the bone foundation guide prosthesis 200 as the bone foundation guide prosthesis 220 moves over the buccal wall 24 for attachment or removal. A fastener channel 226 could traverse the buccal wall 24 and the attachment tab 222 (when inserted into the tab slot 224) to allow removable placement of a strut fastener 49 (not shown) placed into the fastener channel 226 to help hold the anchoring 42 strut to the top 34 of the buccal wall. It should be noted that it may not be necessary for each anchoring strut 42 to have support tab-support slot attachment capability.

Figure 27:
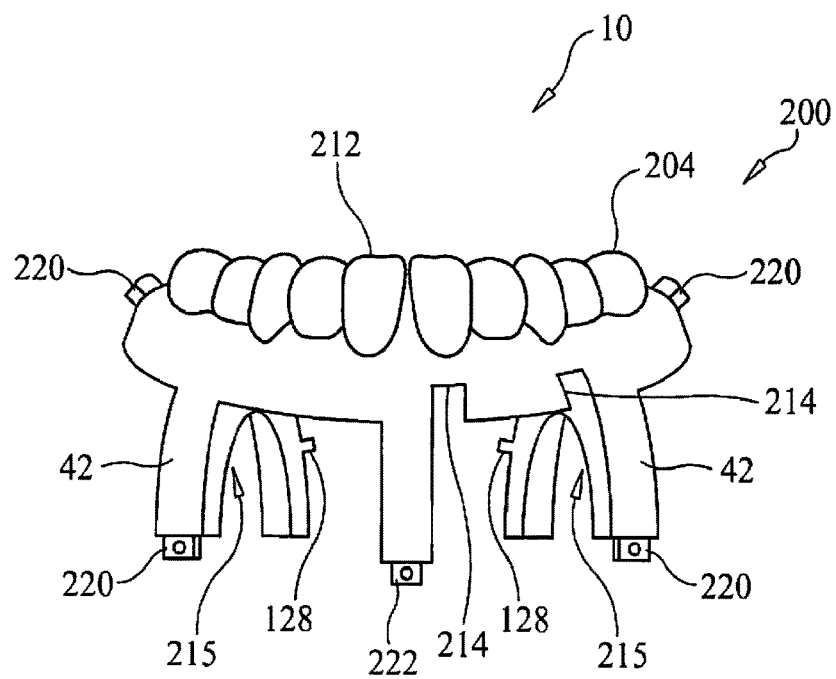
FIG. 27 is substantially a perspective view of the bone foundation guide prosthesis, the prosthesis being unitary with the anchoring struts.
Figure 28:
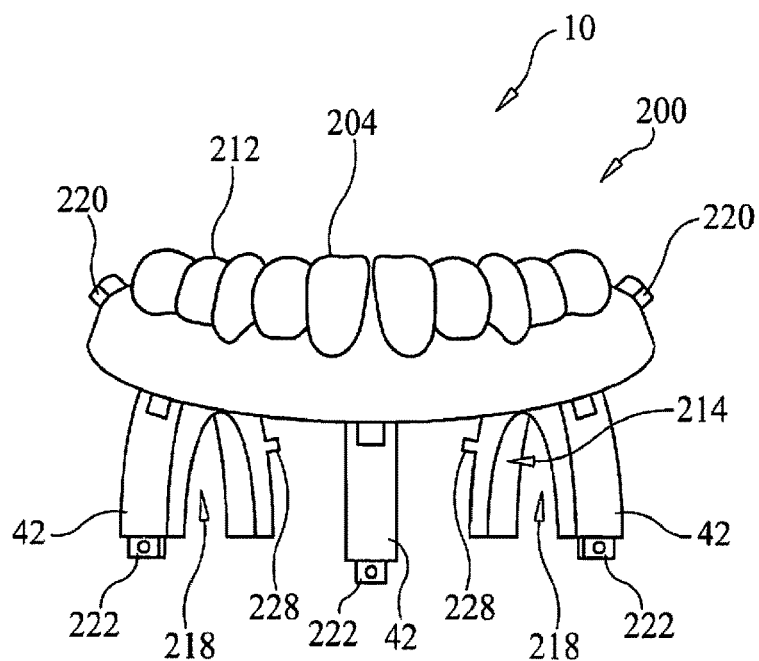
FIG. 28 is substantially a perspective view of the bone foundation guide prosthesis being non-unitary with the anchoring struts.

As substantially shown in FIG. 27, one possible version of the bone foundation guide prosthesis 200 could have the teeth portion 204 be unitary or one-piece with the one or more struts 48 substantially providing strength and rigidity to the combination 202. In another version as substantially shown in FIG. 28, the one or more anchor struts 42 are removably attached to the bottom 214 of the bone foundation guide prosthesis 200. Friction fit based tab-slot coupling means could be utilized to removably attach the removable anchor struts 42 to the bone foundation guide prosthesis 200.

Figure 32:
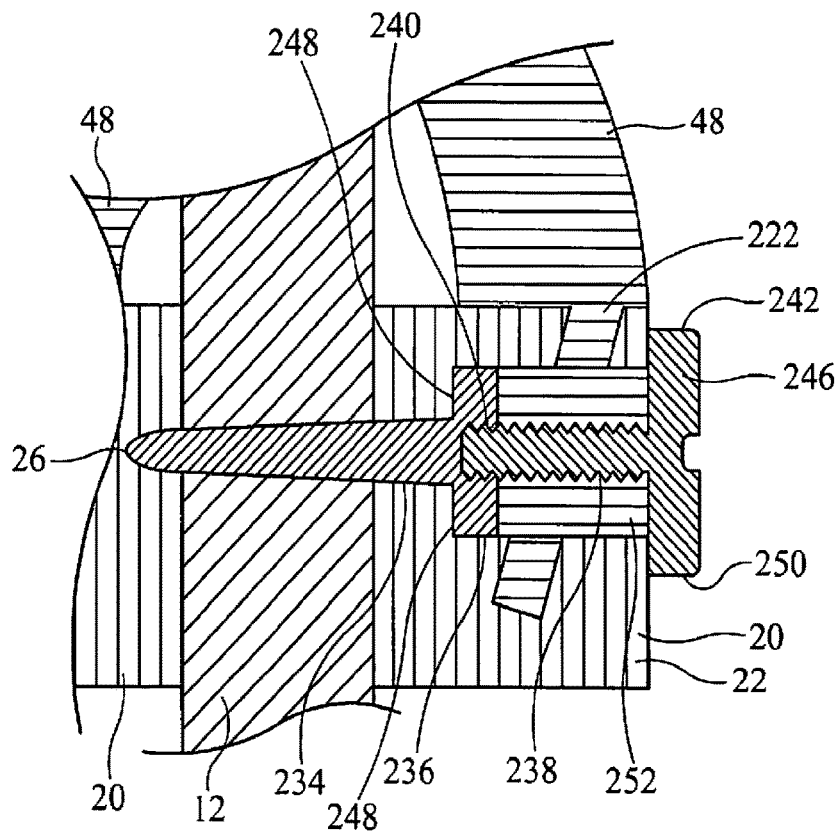
FIG. 32 is substantially a perspective view of multiple piece fastener that can connect a strut to the buccal wall and the buccal wall to the bone segment of the dental implant surgical site to allow a subsequent removal of the strut from the bone foundation guide while retaining the attachment of the buccal wall to the bone segment.

As substantially shown in FIG. 32, one possible embodiment the strut fastener 49 could be a multiple piece strut fastener 232 that could both hold the strut front end 43 to the buccal wall 24 as well as secure the buccal wall 24 to the bone segment 14. The multiple piece strut fastener 232 could have a taper pin 234 comprising a head 236 that could further form a threaded receptacle 238. The threaded receptacle 238 could removably receive a part of a threaded portion 240 of a threaded fastener 242 to removably connect the taper pin 234 to the threaded fastener 242. The fastener head 246 could be larger in diameter than the head 236 of the tapered pin 234 to allow shoulders 248 as provided by the stepped configuration of the fastener channel 226 to support the head 236 of the tapered pin 234. The fastener head 246 could have a serrated edge 250 to allow a pliers or like (not shown) to grasp the threaded fastener 242 to pull out combined threaded fastener and taper pin from the fastener channel 226 (e.g., and from contact the bone segment 12, attachment tab 222, buccal wall 24 and lingual wall 26.) The removal of just the threaded fastener 242 only could leave the tapered pin 234 in place to secure the body 22 to the bone segment 12 while allowing the bone foundation guide prosthesis 200 to be removed from the body 22. A cylinder 252 could be placed on the threaded portion 240 of the threaded fastener 242 to assist the threaded fastener's placement into the fastener channel 226.

As substantially shown in FIGS. 7-26, one possible method or process 100 for the use of the invention could start with step 102, digital scanning and modeling for the patient-specific dental surgery. In this step, dental digital methods (digital dentistry) may be used in creating patient-specific map of the patient's mouth (which could include the digital scanning of analogue appliances such as patient specific castings and impressions); in creating models for patient-specific bone remodeling (e.g., foundation and re-contouring) of the upper and/or lower dental struts in the patient's mouth; in creating models for dental implant surgical guides/bone foundation guides and prosthetics used post-patient-specific bone remodeling; in creating a patient specific model of the patient's mouth post dental surgery. After this step is substantially completed, the process 100 could proceed to step 104, creation of the guides, tissue spacing gasket and other dental appliances.

In step 104, creation of the guides and other dental appliances, the acquired and processed modeling data can be used to create the patient-specific bone foundation guide (e.g., d patient-specific bone foundation guide, tissue spacing gasket and dental implant surgical guide that be stacked together in various combinations. The anchoring struts can also be patient-specific made to have indentations at their respective apexes to match various portions of the dentition, tissue or both of the opposing alveolar ridge. Once manufactured, the anchoring struts could be removably attached to the bone foundation body. The strut fastener (e.g., a tapered pin) could removably attach the anchoring strut's front end to the buccal wall. The strut rear end could removably straddle the cutting guard's respective cutout with the strut groove allowing the strut groove's tab to be removably received within the cutout.

The design and manufacturing imparted stacking capability could allow the two guides and gasket to come together to various stacked combinations. This stacking capability allows the bone foundation guide, once removably secured to the dental surgical site by the dental health care profession, to generally act as foundation for the dental implant surgical guide or the spacing tissue gasket to secure them alternately to the dental surgical site. This stacking capability could allow the implant, implant components, implant instruments and the like to be guided through the dental implant surgical guide implant apertures and the bone foundation guide's open surgical space to properly interact with the dental surgical site. After this step is substantially completed, the process 100 could proceed to step 106, surgical prep.

In step 106, surgical prep, the dental health care professional could (after properly anesthetizes the patient and instituting other required dental surgical pre-operation protocols) could make incisions in the gum area of the dental surgical site, and peel back the gum tissue to expose the portion of bone being operated upon at the dental surgical site. Any teeth at the dental implant surgical site can be removed. If the patient's dental health has declined enough, the alveolar ridge supporting the dental surgical site could be made edentulous After this step is substantially completed, the process 100 could proceed to step 108, use of the bone foundation guide.

In step 108, use of the bone foundation guide, the bone foundation guide could be removably attached to the bone foundation guide prosthesis to generally form the bone foundation guide-bone foundation guide prosthesis combination. For the non-unitary version of the bone foundation guide prosthesis, the anchoring struts could then be attached to the bottom of the teeth portion. The anchoring struts (both for unitary and non-unitary versions of the bone foundation guide prosthesis) could then be moved into place over the bone foundation guide body so that support tabs on the teeth portion and securing tabs near the rear end of the anchoring struts can removably engage their respective slots formed by the lingual wall cutting guard. The front ends of the struts can then be swung down upon the top of the buccal wall of the body of the bone foundation guide to respectively engage the attachment tabs with the attachment tab slots formed by the buccal wall. Suitable fasteners can then be placed into the fastener channels to removably secure the attachment tabs in their respective attachment slots to generally hold the bone foundation guide prosthesis in place upon the body to form the combination. The dental healthcare professional can then initially set the combination upon the bone segment of the dental implant surgical site without first having to remove or alter the bone segment.

The patient could "bite" upon the bone foundation guide prosthesis to bring the opposing alveolar ridge (e.g., the opposing the dentition, tissue or both) into contact with the teeth portion of the combination. By biting upon the combination, the patient generally holds the bone foundation guide initially in place upon the dental implant surgical site. This bite compression could allow the dental healthcare professional to view the resulting bite of the teeth portion and opposing alveolar ridge to help ensure that as the surgical plan is carried out that the final (e.g., implant attached) prosthesis will have the same bite and lockup as one shown by the bone foundation guide prosthesis. This allows the dental healthcare professional to examine the bite as well as resulting orientation, telemetry, positioning, aesthetics and the like as generally provided by the bite. Further, the dental healthcare professional can examine the bone segment and combination interface located below the teeth portion and between the anchoring arches to make sure the combination is properly set upon the bone segment. The dental healthcare professional may also use the cutouts to further examine the bone segment-combination interface.

If the alveolar ridge-teeth portion bite does not result in proper or desired telemetry, positioning, orientation, aesthetics; if the combination cannot fit properly upon the bone segment or both then the dental implant surgery can be halted until such deficiencies can be properly rectified. At that point, the combination can be removed from the bone segment, and gum tissue can be re-sutured up to cover the exposed bone segment. If non-unitary version of the bone foundation guide prosthesis is used, then the teeth portion can be removed from the arches and body. The teeth portion can be attached (e.g., glued or cemented) to a denture base to form a denture. The patent can then use the formed denture until corrections have been made to the aspects of the dental implant surgical plan, models and alike to allow the dental implant surgery to resume.

If the alveolar ridge-teeth portion bite results in proper or desired telemetry, positioning, orientation, aesthetics and if the combination fits properly upon the bone segment or then dental implant surgery can proceed with the dental healthcare professional with both hands free to use a drill to make channels in the dental surgical site (e.g., the exposed bone portion) utilizing the attachment apertures. Body fasteners are placed into the attachment apertures and channels to generally removably attach the bone foundation guide to the exposed bone at the dental surgical site. If multiple piece fasteners are used, those fasteners can further secure the through the fastener attachment of the buccal wall through the bone segment to the lingual wall of the bone foundation guide. The dental healthcare professional asks the patient to relax its grip upon the bone foundation guide to generally bring the portion of the dentition, tissue or both of the opposing alveolar ridge out of contact with the indentation(s). When the anchoring struts are cleared from the body (e.g., the threaded fasteners are removed), the bone foundation guide prosthesis could be removed from the bone foundation guide.

The removal of bone foundation guide prosthesis could clear the bone foundation guide to allow the bone foundation guide top to be used to guide a cutting implement (e.g., blade saw) to reduce the dental implant surgical site's bone structure. The harvested bone (e.g., or bone analogue) could then be used to augment the dental surgical site if needed. Known dental techniques for reducing or augmenting the bone could be employed to provide the proper bone contour for the dental implant surgical site. Once this step is substantially completed, the process 100 could proceed to step 110, use of the dental implant surgical guide.

In step 110, use of the dental implant surgical guide, the dental health care professional could place the bottom side of the dental implant surgical guide upon the top of the bone foundation guide generally enclosing the open surgical space. In one embodiment, the tissue spacing gasket is sandwiched between the bone foundation guide and the dental implant surgical guide. Pins on the underside of the dental implant surgical guide could attach to the attachment apertures in the bone foundation guide top (e.g., by the buccal wall) while the guide tabs extending out from the lingual side could removably engage the cutting guard cutouts to provide a snap fit of the dental implant surgical guide into the bone foundation guide.

The dental healthcare professional could use the bone foundation guide and the dental implant surgical guide stacked or otherwise combined together to substantially direct and operate implant preparation implements (e.g., drills, reamers, and the like), implant components, or both by passing them through the dental implant surgical guide and into the open surgical space to properly prepare the dental surgical site to receive the implant(s) This implant preparation could ensure there was proper orientation and telemetry of the implant components and implants into the generally exposed bone of the dental surgical site. Once the bone is properly prepared to receive the implants, the implant(s) could then pass through the combination to be anchored into the bone. Once this step is substantially completed, the process 100 could proceed to step 112, using tissue spacing gasket.

In step 112, using tissue spacing gasket, once the implants were properly located and set within the dental surgical site, the surgical implant dental guide could be removed from the bone foundation guide and the tissue spacer gasket could alternatively be connected to the bone foundation guide. In one embodiment, the pins located on the gasket bottom can be generally be removably received in the same apertures on the bone foundation guide top that the accommodated the guide pins of the dental implant surgical guide.

In one possible embodiment, once the tissue spacing gasket is removably attached to the bone foundation guide then temporary abutments can be placed upon the implants. A temporary prosthesis can be placed over the tissue spacer gasket to come into contact the temporary abutments. The tissue spacing gasket could cradle the temporary prosthesis at this point holding it in the proper vertical and concentric orientation as dental acrylic is injected into the temporary prosthesis to secure the abutments to the temporary prosthesis. The tissue spacing gasket may further prevent the acrylic from leaking upon and contaminating the exposed bone. The tissue spacing gasket may as well as prevent any acrylic leaking onto the abutment undercut (e.g., to generally prevented unwanted premature attachment of the prosthesis to the implants.) The tissue spacing gasket may help to insure that proper distance between bone and prosthesis is maintained to account for presence of tissue when the gum tissue is placed back over the bone.

Once the acrylic has set, the above abutment prosthesis attachment process may repeated used for a clear or analogue prosthesis that later can be sent back to the lab. The analogue prosthesis with its affixed abutments may be applied to implant bone model that was devised through the dental model to see how the dental healthcare professional may have deviated from the original dental surgical plan in attaching the implants to the dental surgical site. In that manner, the analogue prosthesis will allow the final changes of the actual dental surgery (on site changes made by the dental healthcare professional to take into account issues not foreseen by the dental surgical plan) to be imparted onto the dental model and to the final prosthesis.

Once the temporary prosthesis (and analogue prosthesis) is removed from the tissue spacing gasket-bone foundation guide combination, the tissue spacing gasket could be removed from the bone foundation guide. The gum tissue flaps could be sutured back over the exposed bone (but not necessarily over the implants) and the temporary prosthesis could be reattached to the implants. As the dental surgical site heals and the implants further incorporate themselves into the bone structure, the temporary prosthesis could help maintain the implant positioning as set during the surgery, so that the permanent prosthesis should be able to replace the temporary prosthesis with minimal adjustment and fitting.

This process 100 could also allow as needed, use of temporary cylinder, associated seals, additional filling, and other sealing methods that may be used to properly prepare the dental implant for the attachment of prosthesis and the like. If healing abutments are used instead, then they can be fitted to the implants as needed. The gum tissues can then be sutured or otherwise cover-up the exposed bone to meet up with the abutment/implants. If the gum tissues need to heal or need to heal around the healing abutments or the implants require ossification to secure them in place to the bone, then after these event(s) have occurred/or a suitable amount of healing time has passed then the final prosthesis (or prosthetic) could be placed upon the implants in a secure fashion. After this step is substantially completed, the process 100 could proceed back to step 102 as needed.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As shown in the specification, drawings, claims and abstract, the invention, a bone foundation guide provides for the combining a bone foundation guide and a bone guide foundation prosthesis and a method of use for the resulting combination. The prosthesis can have a teeth portion representing a bite of a final prosthesis as well as one or more anchoring struts that removably attach the prosthesis to the bone foundation guide. The patient could apply the opposing alveolar ridge to the teeth portion to hold the combination in place upon the bone segment of the dental implant surgical site as well as check the bite of the teeth portion and alveolar ridge. The action allows the dental healthcare professional check in situ the representation or analogue of final prosthesis with opposing alveolar ridge to detect any inconsistency or deviation from the dental implant surgical plan. If any inconsistence or deviation is detected, the combination can be removed from the dental implant surgical site prior to any bone removal; the gum tissue can be re-sutured and the patent can use a denture formed from the teeth portion attached to a denture base while inconsistence or deviation are being suitably addressed. If no significant deviation or inconsistency is detected, the dental implant surgery can proceed with the attachment of the combination to the dental implant surgical site; the removal of the prosthesis from the bone foundation guide; and the removal of bone from the dental implant surgical site.

What is claimed is:

1. A bone foundation guide system comprising:
   A) a bone foundation guide comprising a body having a buccal wall and a lingual wall that is continuously connected by a first end and a second end forming an open surgical space connecting a top of the body with a bottom of the body, wherein the bottom is contoured to removably affix the body to a bone segment of a dental implant surgical site, wherein the body is further contoured to guide cutting of a portion of the bone segment from the dental implant surgical site, wherein the body is further configured to support a dental implant surgical guide;
   B) a bone foundation guide prosthesis, wherein the body is further configured to support the bone foundation guide prosthesis in place of the dental implant surgical guide, wherein the bone foundation guide prosthesis is configured to combine with the body and define a space, adjacent to the open surgical space, that is configured to accommodate a portion of the bone segment protruding through the open surgical space of the body and into the space defined by the bone foundation guide prosthesis; and
   C) one or more anchoring struts that are configured to removably connect the bone foundation guide prosthesis to the body by further connecting the buccal wall to the lingual wall.

2. A bone foundation guide system of claim 1 wherein the bone foundation guide prosthesis further has a teeth portion that replicates a teeth structure of a final prosthesis.

3. A bone foundation guide system of claim 1 wherein the bone foundation guide prosthesis and bone foundation guide combination can receive at least a portion of an alveolar ridge opposing the dental implant surgical site.

4. The bone foundation guide system of claim 1 wherein the bone foundation guide prosthesis is unitary with the one or more anchoring struts.

5. The bone foundation guide system of claim 1 wherein at least one of the one or more anchoring struts is configured to further connect to a bottom of the bone foundation guide prosthesis.

6. The bone foundation guide system of claim 1 further comprising one or more multiple piece strut fasteners that are configured to pass through the one or more anchoring struts to removably attach the one or more anchoring struts to the body and the body to the bone segment.

7. The bone foundation guide system of claim 1 wherein each anchoring strut has an angled tab that is removably received within an angled tab slot formed by the buccal wall, wherein both the angled tab and angled slot are configured to removably receive a respective fastener.

8. The bone foundation guide system of claim 1 wherein the bone foundation guide prosthesis is configured to directly contact the body proximate to the first end and the second end body ends.

9. A bone foundation guide system of claim 1 wherein the bone foundation guide prosthesis is configured to combine with the body and thereby form three points of contact with the portion of the bone segment as that portion of the bone portion is placed within the body.

10. A method of operating a bone foundation guide system comprising the following steps:
(A) providing a bone foundation guide comprising a body having a buccal wall and a lingual wall that is continuously connected by a first end and a second end forming an open surgical space that further connects a top of the body with a bottom of the body;
(B) providing a bone foundation guide prosthesis, wherein the bone foundation guide prosthesis has a body;
(C) combining the body of the bone foundation guide with the bone foundation guide prosthesis via one or more anchoring struts that are configured to removably connect the bone foundation guide prosthesis to the body of the bone foundation guide by further connecting the buccal wall to the lingual wall, wherein the combination defines a gap between the body of the bone foundation guide and the body of the bone foundation guide prosthesis; and
(D) placing the combination upon a bone segment of a dental implant surgical site, wherein a portion of the bone segment passes through the open surgical space of the body as the combination is placed upon the bone segment, wherein the portion of the bone segment is further received in the gap of the combination as the combination is placed upon the bone segment.

11. The method of claim 10 further comprising a step of removably receiving an opposing alveolar arch onto the combination.

12. The method of claim 11 wherein the step of removably receiving the opposing alveolar arch further comprises a step of examining a bite of the opposing alveolar ridge to the bone foundation guide prosthesis by checking one bite parameter from a set of bite parameters consisting of positioning, telemetry, orientation and aesthetics.

13. The method of claim 11 wherein the step of removably receiving the opposing alveolar arch further comprises a step of removably receiving the opposing alveolar arch onto a teeth portion of the bone foundation prosthesis.

14. The method of claim 10 further comprising a step of removing the bone foundation guide prosthesis from the body of the bone foundation guide as attached to the dental implant surgical site to clear the bone foundation guide for guiding the removal of the bone segment portion from a dental implant surgical guide.

15. The method of claim 14 wherein the step of removing the bone foundation guide prosthesis from body of the bone foundation guide further comprises a step of removing the one or more anchoring struts from the bone foundation guide prosthesis.

16. The method of claim 10 further comprising a step of removing a teeth portion from the bone foundation guide prosthesis.

17. The method of claim 16 wherein the step of removing a teeth portion further comprises a step of combining the teeth portion with a denture base to form a denture.

\* \* \* \* \*